United States Patent [19]
Srinivasa et al.

[11] Patent Number: 5,998,617
[45] Date of Patent: Dec. 7, 1999

[54] ELECTROCHROMIC COMPOUNDS

[75] Inventors: Ramanujan Srinivasa; Darla J. French; Rongguang Lin; Thomas F. Guarr; Harlan J. Byker; Kelvin L. Baumann, all of Holland; David A. Theiste, Byron Center, all of Mich.

[73] Assignee: Gentex Corporation, Zeeland, Mich.

[21] Appl. No.: 08/831,809

[22] Filed: Apr. 2, 1997

[51] Int. Cl.$^6$ ................................................. C07D 241/46
[52] U.S. Cl. ............................................................. 544/347
[58] Field of Search ............................................. 544/347

[56] References Cited

U.S. PATENT DOCUMENTS

| | | | |
|---|---|---|---|
| 4,902,108 | 2/1990 | Byker | 350/357 |
| 5,140,455 | 8/1992 | Varaprasad et al. | 359/275 |
| 5,294,376 | 3/1994 | Byker | 252/600 |
| 5,500,760 | 3/1996 | Varaprasad et al. | 359/272 |
| 5,698,709 | 12/1997 | Rhubright et al. | 548/447 |

FOREIGN PATENT DOCUMENTS 1031346  5/1978  Canada .

OTHER PUBLICATIONS

Cheng et. al., "Benzidine Rearrangements. XIII . . . ", J. Org. Chem., vol. 40, No. 6, pp. 703–710, Mar. 21, 1975.
A. Sugimoto et al., Preparation and Properties of Electron Donor Acceptor Complexes of the Compounds having Capto–dative Substituents, J. Heterocyclic Chem., 26, 435 (1989), pp. 435–438.
S. Flandrois et al., Structure and Paramagnetism of Strong Charge–Transfer Complexes: 5.10–Dihydro–2.3.5.7.8.10–hexamethyl–phenazine–tetracyanoethylene $(M_6P)(TCNE)$, Mol. Cryst. Liq. Cryst., 1983, vol. 95, pp. 149–164.
W. Radeck, Preparation of polyfluorinated N,N—disubstituted phenazines, Chem Abstracts114: 102059r, 1991.
J. A. Barltrop et al., The synthesis and Electrochemical Study of New Electrochromic Viologen–based Materials, J. Chem. Soc. Perkin Trans. II 1984 pp. 367–371.
H. J. Keller et al., Solid Charge–Transfer Complexes of Phenazines, Top. Curr. Chem. 1985 127 (Org. Chem.) pp. 169–216, see especially p. 193.
S. P. Schmidt et al. Chemiluminescence of Dimethyldioextanone. Unimolecular Generation of Exited Singlet and Triplet Acetone. Chemically Initiated Electron–Exchange Luminescence, the Primary Light Generating Reaction, Journal of the American Chemical Society, 102:1, 1980 pp. 206–314.
G. B. Schuster et al., Photophysics of N,N–Dimethyldihydrophenazine and Benzoannelated Analogues, Structurally Dependent Excited–State Hierarchy, J. Phys. Chem. 1980, 84, 1841–1843.
Axel Kistenmacher et al., Synthesis of New Soluble Triphenodithiazines and Investigation of Their Donor Properties, Chem. Ber. 1992, 125, 1495–1500.
Hisao Nishi et al., Thermal Formation of Triphenodithiazinequinone and Triphenodiselenazinequinone, J. Heterocyclic Chem. 1989, 26, 875–876.

*Primary Examiner*—Mukund J. Shah
*Assistant Examiner*—Tamthom N. Truong
*Attorney, Agent, or Firm*—Brian J. Rees

[57] ABSTRACT

An improved electrochromic device, the device incorporating an electrochromic medium that comprises at least three electroactive materials having absorption spectra that add together such that the color of the electrochromic medium can be pre-selected by individually choosing the concentrations of the at least three electroactive materials. The electrochromic medium generally maintains the pre-selected perceived color throughout its normal range of voltages when used in an electrochromic device. The at least three electroactive materials include at least one electrochemically reducible material (cathodic material), at least one electrochemically oxidizable material (anodic material) and at least one additional electroactive material which may be either an anodic or cathodic material. Thus, there are always three electroactive materials present in the medium, with at least two either being anodic or cathodic materials. The pre-selected color may be chosen from a wide variety of colors and may be, for example, red, orange, yellow, green, blue, purple. For electrochromic mirrors for motor vehicles, a presently preferred color is gray.

20 Claims, 4 Drawing Sheets

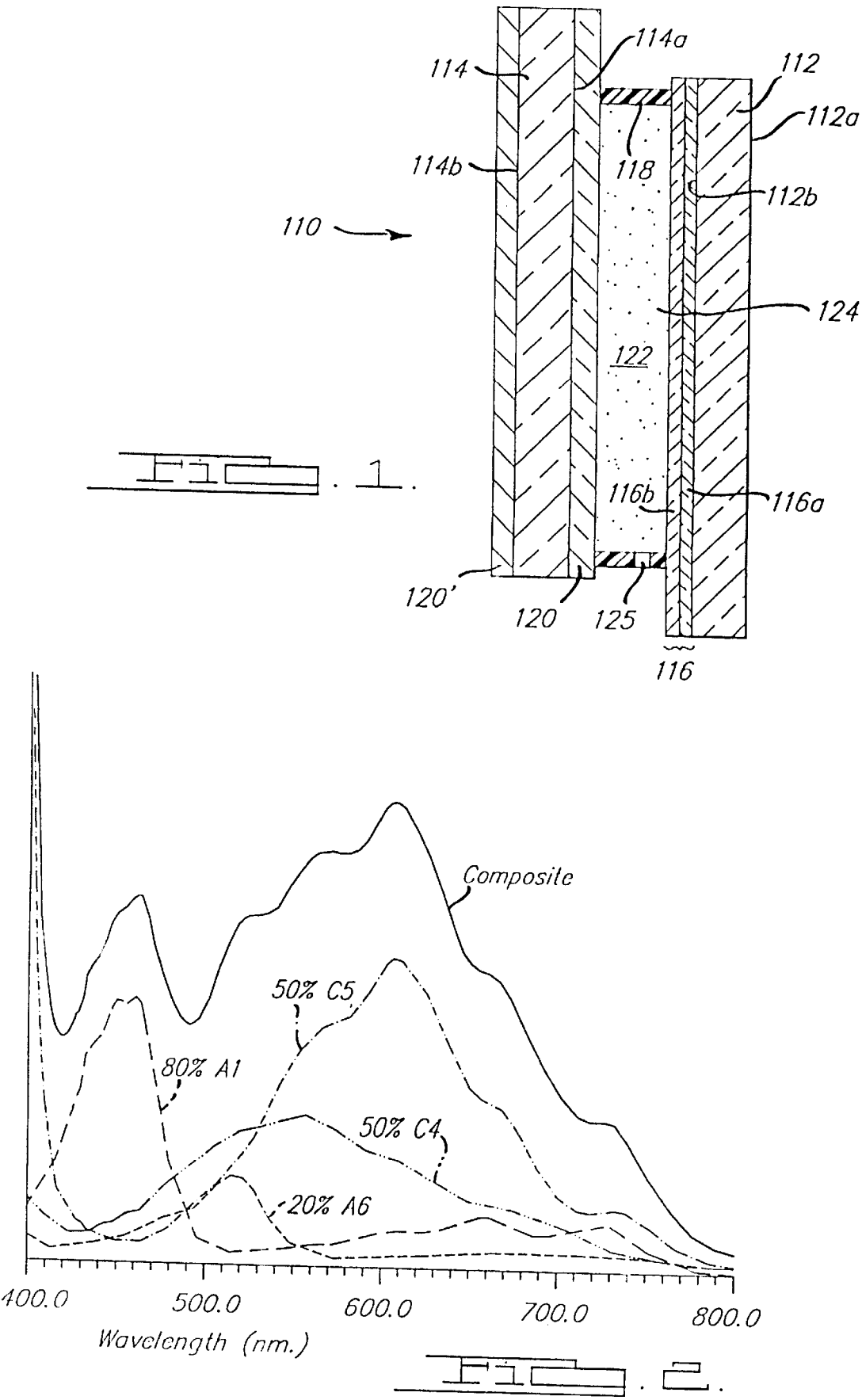

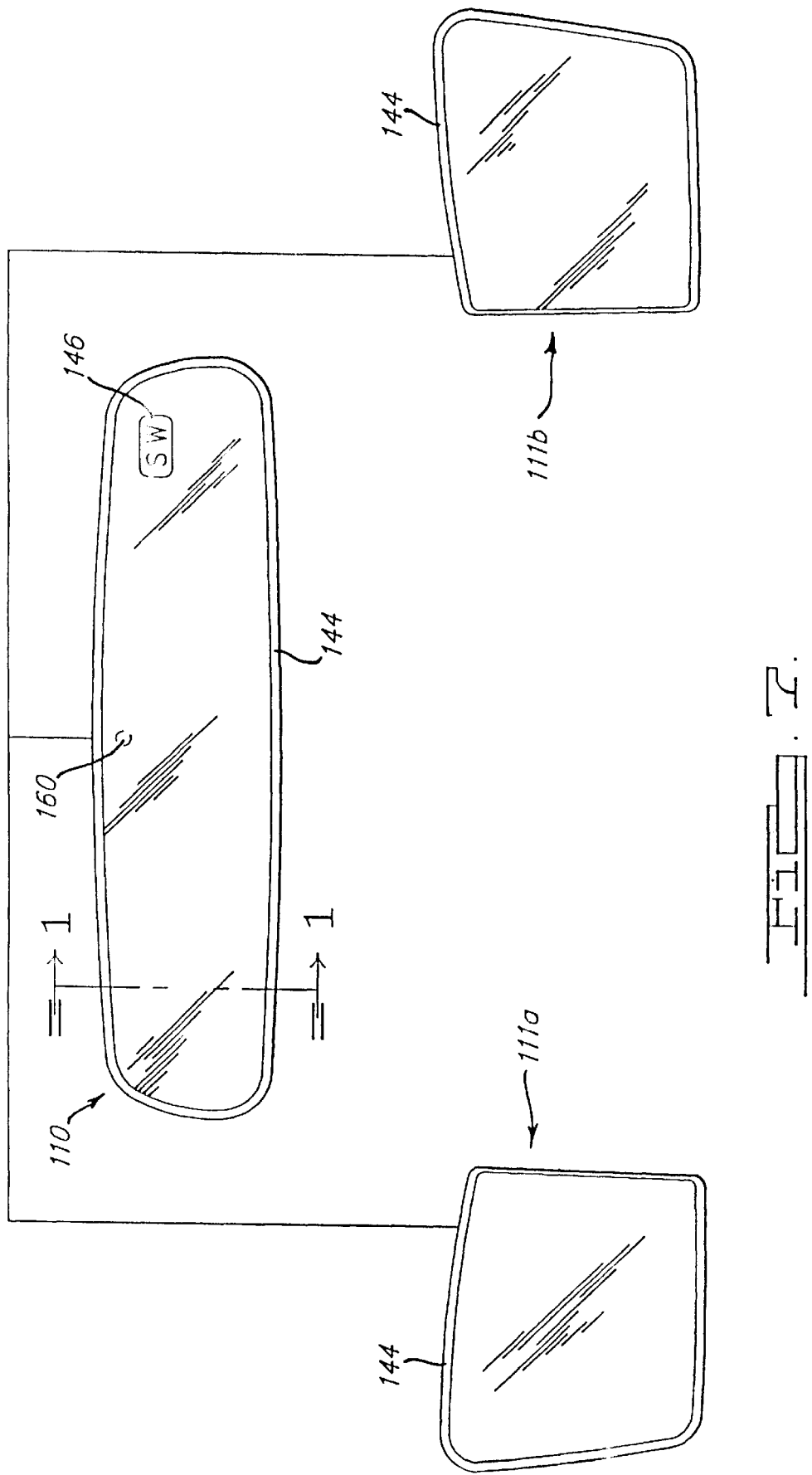

ELECTROCHROMIC COMPOUNDS

BACKGROUND OF THE INVENTION

This invention relates to an improved electrochromic medium capable of producing a pre-selected color and, more particularly, an improved electrochromic device having an electrochromic medium comprising at least three electroactive materials whose concentrations may be chosen to produce a pre-selected perceived color, where the electrochromic medium generally maintains the pre-selected perceived color throughout its normal range of voltages when used in an electrochromic device.

Electrochromic devices have been proposed for commercial applications for nearly seventy years (British Patent Specification No. 328,017 (1929) to F. H. Smith). However, the first commercially successful electrochromic device, a dimmable rearview mirror for motor vehicles, was not introduced until 1987. Various automatic rearview mirrors for motor vehicles have been devised which automatically change from the full reflectance mode (day) to the partial reflectance mode(s) (night) for glare protection purposes from light emanating from the headlights of vehicles approaching from the rear. The electrochromic mirrors disclosed in U.S. Pat. No. 4,902,108, entitled "Single-Compartment, Self-Erasing, Solution-Phase Electrochromic Devices, Solutions for Use Therein, and Uses Thereof", issued Feb. 20, 1990 to H. J. Byker; Canadian Patent No. 1,300,945, entitled "Automatic Rearview Mirror System for Automotive Vehicles", issued May 19, 1992 to J. H. Bechtel et al.; U.S. Pat. No. 5,128,799, entitled "Variable Reflectance Motor Vehicle Mirror", issued Jul. 7, 1992 to H. J. Byker; U.S. Pat. No. 5,202,787, entitled "Electro-Optic Device", issued Apr. 13, 1993 to H. J. Byker et al.; U.S. Pat. No. 5,204,778, entitled "Control System For Automatic Rearview Mirrors", issued Apr. 20, 1993 to J. H. Bechtel; U.S. Pat. No. 5,278,693, entitled "Tinted Solution-Phase Electrochromic Mirrors", issued Jan. 11, 1994 to D. A. Theiste et al.; U.S. Pat. No. 5,280,380, entitled "UV-Stabilized Compositions and Methods", issued Jan. 18, 1994 to H. J. Byker; U.S. Pat. No. 5,282,077, entitled "Variable Reflectance Mirror", issued Jan. 25, 1994 to H. J. Byker; U.S. Pat. No. 5,294,376, entitled "Bipyridinium Salt Solutions", issued Mar. 15, 1994 to H. J. Byker; U.S. Pat. No. 5,336,448, entitled "Electrochromic Devices with Bipyridinium Salt Solutions", issued Aug. 9, 1994 to H. J. Byker; U.S. Pat. No. 5,434,407, entitled "Automatic Rearview Mirror Incorporating Light Pipe", issued Jan. 18, 1995 to F. T. Bauer et al.; U.S. Pat. No. 5,448,397, entitled "Outside Automatic Rearview Mirror for Automotive Vehicles", issued Sep. 5, 1995 to W. L. Tonar; and U.S. Pat. No. 5,451,822, entitled "Electronic Control System", issued Sep. 19, 1995 to J. H. Bechtel et al., each of which patents is assigned to the assignee of the present invention and the disclosures of each of which are hereby incorporated herein by reference, are typical of modern day automatic rearview mirrors for motor vehicles. Such electrochromic mirrors may be utilized in a fully integrated inside/outside rearview mirror system or as an inside or an outside rearview mirror system. In general, in automatic rearview mirrors of the types disclosed in the above referenced U.S. Pat.s, both the inside and the outside rearview mirrors are comprised of a relatively thin electrochromic medium sandwiched and sealed between two glass elements.

In most electrochromic mirrors, when the electrochromic medium which functions as the media of variable transmittance is electrically energized, it darkens and begins to absorb light, and the more light the electrochromic medium absorbs the darker the mirror becomes. When the electrical voltage is decreased to zero, the mirror returns to its clear state. The electrochromic medium is contained in a sealed chamber defined by a transparent front glass element coated with a transparent conductor, a peripheral edge seal, and a rear mirror element having either a reflective layer or a transparent conductive layer in contact with the electrochromic medium depending on whether the mirror has a third or fourth surface reflector. The conductive layers on both the front glass element and the rear glass element are connected to electronic circuitry which is effective to electrically energize the electrochromic medium to switch the mirror to nighttime, decreased reflectance modes when glare is detected and thereafter allow the mirror to return to the daytime, high reflectance mode when the glare subsides, as described in detail in the aforementioned U.S. Patents. For clarity of description of such a structure, the front surface of the front glass element is referred to as the first surface, and the inside surface of the front glass element is referred to as the second surface. The inside surface of the rear glass element is referred to as the third surface, and the back surface of the rear glass element is referred to as the fourth surface.

The electrochromic medium is typically comprised of solution-phase electrochromic materials, electrodeposition type electrochromic materials, surface confined electrochromic materials or combinations thereof. The electrochromic medium changes from a clear or high visible light transmission level, to a lightly colored state, to a moderately colored state, and to a dark or low visible light transmission colored state when various voltages are applied and electrochemical oxidation and reduction take place. An important factor in determining the desirability of an electrochromic device is its perceived color when in its clear state and dark state and any state therebetween. The perceived color of an electrochromic mirror includes the influences from the front glass element, the two transparent conductive coatings, the reflector and, most importantly, the electrochromic medium.

Generally speaking, there is a desire for a gray colored electrochromic medium in interior mirrors and most exterior mirrors for motor vehicles because the perceived color of the reflected image will closely resemble the color of the object before being reflected. In addition, it is desirable that the electrochromic device maintain this gray color during its darkening and clearing transitions so that the perceived colors of a reflected image do not change during these transitions. However, arguments have been made for tinted or colored mirrors. For example, commonly assigned U.S. Pat. No. 5,278,693 to D. A. Theiste et al., discloses adding an electrochemically inactive and stable compound to a solution-phase electrochromic device to provide a blue tint. This electrochemically inactive compound is essentially a dye normally present at low levels, and will provide a perceived tint to the device only in the highest reflectance or transmittance states when little or no voltage is applied.

In other applications such as architectural windows, sun roofs, displays and specialty windows, various colors (e.g., blue, greens, purples, yellows) in addition to gray may be desirable for a number of reasons. For instance, it may be desired that certain electrochromic windows be tinted to match the decor of the room, provide contrast enhancement or gray scale dimming filters for displays emitting particular colors of light, or to give a building a particular color or appearance.

A problem in the art, then has been the inability to pre-select a color of an electrochromic device while simultaneously ensuring that the device generally maintains the desired color when in its clear state and dark state and any state therebetween. With such devices used as electrochromic rearview mirrors for motor vehicles and many window applications, a desired color is one that is perceived as gray. For other applications, colors that are perceived other than gray, (e.g., red, yellow, green, blue, purple) may be desirable.

Consequently, it is desirable to provide an improved electrochromic medium having at least three electroactive materials whose concentrations may be chosen to produce a pre-selected perceived color, where the electrochromic medium generally maintains the pre-selected perceived color throughout its normal range of voltages when used in an electrochromic device.

OBJECTS OF THE INVENTION

Accordingly, a primary object of the present invention is to provide an improved electrochromic medium having at least three electroactive materials whose relative concentrations may be chosen to produce a pre-selected perceived color, where the electrochromic medium generally maintains the pre-selected perceived color throughout its normal range of voltages when used in an electrochromic device.

Another object of the present invention is to provide an improved electrochromic medium having at least three electroactive materials whose concentrations may be chosen to produce a perceived gray color, where the electrochromic medium generally maintains the gray color throughout its normal range of voltages when used in an electrochromic device.

Yet another object of the present invention is to provide novel electroactive materials.

SUMMARY OF THE INVENTION

The above and other objects, which will become apparent from the specification as a whole, including the drawings, are accomplished in accordance with the present invention by providing an electrochromic device having an electrochromic medium that comprises at least three electroactive materials having absorption spectra that add together such that the color of the electrochemically activated electrochromic medium can be pre-selected by individually choosing the concentrations of the at least three electroactive materials. The electrochromic medium generally maintains the pre-selected perceived color throughout its normal range of voltages when used in an electrochromic device. The at least three electroactive materials include at least one electrochemically reducible material (cathodic material), at least one electrochemically oxidizable material (anodic material) and at least one additional electroactive material which may be either an anodic or cathodic material. Thus, there are always at least three electroactive materials present in the medium, with at least two either being anodic or cathodic materials. The pre-selected color may be chosen from a wide variety of colors and may be, for example, gray, red, orange, yellow, green, blue, and purple. For electrochromic mirrors for motor vehicles and many window applications, a presently preferred color is gray.

BRIEF DESCRIPTION OF THE DRAWINGS

The subject matter which is regarded as the invention is particularly pointed out and distinctly claimed in the concluding portion of the specification. The invention, together with further objects and advantages thereof, may best be understood by reference to the following description taken in connection with the accompanying drawings, where like numerals represent like components, in which:

FIG. 1 is an enlarged cross-sectional view of an electrochromic device;

FIG. 2 illustrates scaled absorption spectra for the electrochemically activated states of the following individual electrochromic materials: 5,10-dimethyl-5,10-dihydrophenazine (A1); 2,7-diphenoxy-5,10-dimethyl-5,10-dihydrophenazine (A6); 1,1'-dimethyl-4,4'-(1,3,5-triazine-2,4-diyl) dipyridinium diperchlorate (C4); 1,1'-dimethyl-2-(3-phenyl(n-propyl))-4,4'-dipyridinium bis (hexafluorophosphate) (C5), where each absorption spectrum is scaled to the relative concentrations of the activated states that would be present in an activated device; as well as the composite spectrum for the activated state of an electrochromic medium originally comprising A1 and 80% and A6 at 20% of the total anodic materials, plus C4 at 50% and C5 at 50% of the total cathodic materials;

FIG. 7 is a front elevational view schematically illustrating an inside/outside electrochromic rearview mirror medium for motor vehicles where the inside and outside mirrors incorporate the mirror assembly of the present invention.

DETAILED DESCRIPTION

Figure 3:
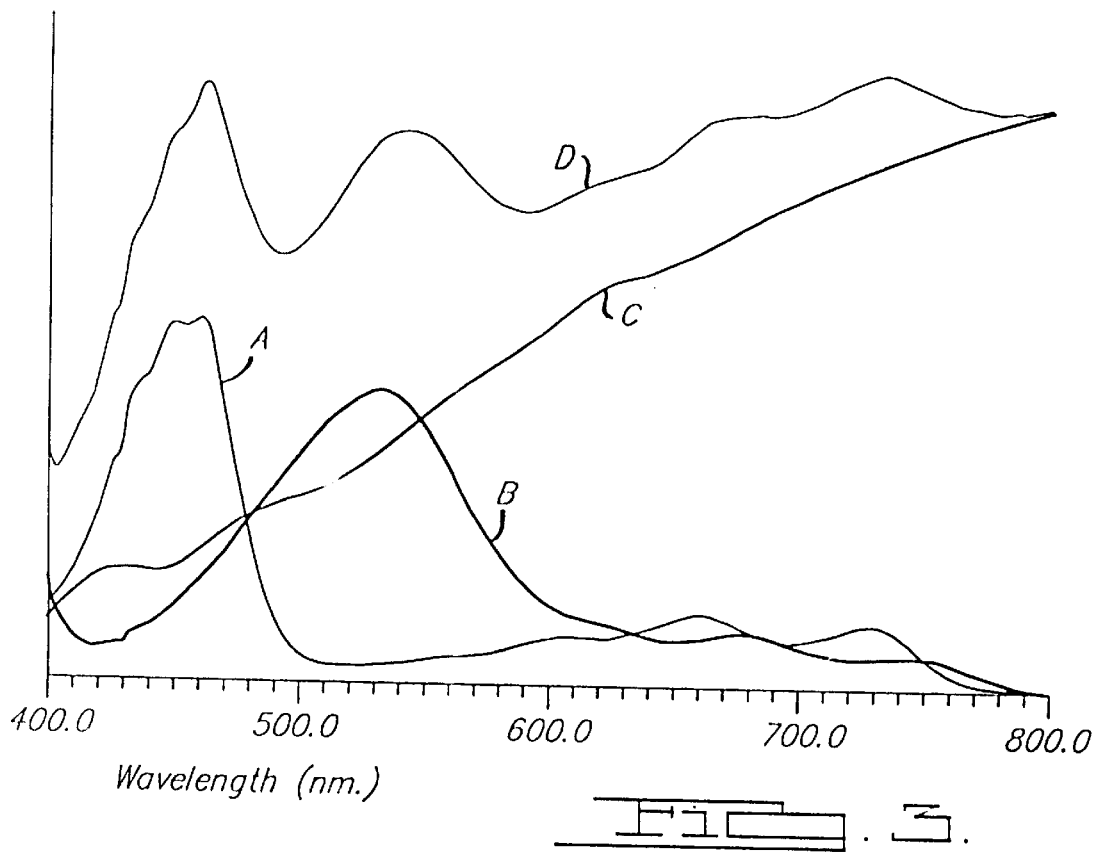
FIG. 3 illustrates scaled absorption spectra for the electrochemically activated states of the following individual electrochromic materials: 5,10-dimethyl-5,10-dihydrophenazine (A); 2,3-diphenyl-5,10-dimethyl-5,10-dihydrophenazine (B); and tungsten trioxide (C), where each absorption spectrum is scaled to the relative concentrations of the activated states that would be present in an activated device; as well as the composite spectrum (D) which is the sum of the scaled spectra of the activated states of these three electrochromic materials.

FIG. 1 shows a cross-sectional view of an electrochromic device 110 which may be a mirror, a window, a display device, and the like. Device 110 has a front transparent element 112 having a front surface 112a and a rear surface 112b, and a rear element 114 having a front surface 114a and a rear surface 114b. Since some of the layers of the mirror are very thin, the scale has been distorted for pictorial clarity. Also, for clarity of description of such a structure, the following designations will be used hereinafter. The front surface 112a of the front glass element will be referred to as the first surface and the back surface 112b of the front glass element as the second surface. The front surface 114a of the rear glass element will be referred to as the third surface, and the back surface 114b of the rear glass element as the fourth surface.

Front transparent element 112 may be any material which is transparent and has sufficient strength to be able to operate in the conditions, e.g., varying temperatures and pressures, commonly found in the automotive environment. Front element 112 may comprise any type of borosilicate glass, soda lime glass, float glass or any other material, such as, for example, a polymer or plastic, that is transparent in the visible region of the electromagnetic spectrum. Front element 112 is preferably a sheet of glass with a thickness ranging from 0.5 millimeters (mm) to about 12.7 mm. Rear element 114 must meet the operational conditions outlined above, except that if the electrochromic device is a mirror, rear element 114 does not need to be transparent, and therefore may comprise polymers, metals, glass, ceramics, and preferably is a sheet of glass with a thickness ranging from 0.5 mm to about 12.7 mm.

A layer of a transparent electrically conductive material 116 is deposited on the second surface 112b to act as an electrode. Transparent conductive material 116 may be any material that: is substantially transparent to visible light; bonds well to front element 112 and maintains this bond when the epoxy seal 118 bonds thereto; is resistant to corrosion by any materials within the electrochromic device; is resistant to corrosion by the atmosphere; and has minimal diffuse or specular reflectance and good electrical conductance. Transparent conductive material 116 may be fluorine doped tin oxide (FTO), tin doped indium oxide (ITO), ITO/metal/ITO (IMI) as disclosed in "Transparent Conductive Multilayer-Systems for FPD Applications", by J. Stollenwerk, B. Ocker, K. H. Kretschmer of LEYBOLD AG, Alzenau, Germany, and the materials described in above-referenced U.S. Pat. No. 5,202,787, such as TEC 20 or TEC 15, available from Libbey Owens-Ford Co. (LOF) of Toledo, Ohio. Co-filed U.S. Patent Application entitled "AN IMPROVED ELECTRO-OPTIC DEVICE INCLUDING A LOW SHEET RESISTANCE, HIGH TRANSMISSION TRANSPARENT ELECTRODE" describes a low sheet resistance, high transmission, scratch resistant transparent electrode that forms strong bonds with adhesives, is not oxygen sensitive, and can be bent to form convex or aspheric electro-optic mirror elements or tempered in air without adverse side effects. The disclosure of this commonly assigned Applications is hereby incorporated herein by reference. Similar requirements are needed for the layer 120 deposited onto the third surface 114a, whether it is a transparent conductive material used in electrochromic windows and in mirrors having a fourth surface reflector, or a combined reflector/electrode (discussed below) used in electrochromic mirrors having a third surface reflector.

The conductance of the layer(s) of transparent conductive material (116 and/or 120) will depend on their thickness and composition. As a general rule TEC coatings from LOF are more color neutral than simple FTO and ITO coatings. This difference in color neutrality impacts the overall color of the reflected image when the mirror is fully darkened because almost all the reflection seen by the driver comes from the first and second surfaces. Thus, if there is transparent conductive material on the second surface of the mirror that is not color neutral it can impact the color of the reflected image viewed by the driver. In certain automotive mirror systems it is beneficial to use TEC coatings as the transparent conductor on the interior mirror, but not larger exterior mirrors. When thin glass is used for larger exterior mirrors TEC cannot be used because these coatings are applied on the float-line, and it is very difficult to make thin glass on large float-lines and even more difficult to apply coatings while making thin glass on a float-line. Therefore, thin glass coated on a float-line is not presently commercially available. If a simple ITO coating is used on the exterior mirror then the reflected image will not be color neutral when the mirror is in the fully darkened state and one will notice a difference in color between the reflected images of these exterior mirror and interior mirrors made with TEC glass coatings. U.S. Patent Application entitled "A ELECTROCHROMIC MIRROR WITH TWO THIN GLASS ELEMENTS AND A GELLED ELECTROCHROMIC MEDIUM" discloses a preferred color neutral transparent conductive coating that can be used on the second surface of a mirror or a window and will eliminate the described problem. The entire disclosure of this commonly assigned co-pending U.S. Patent Application is hereby incorporated herein by reference. This color neutral transparent conductive coating provides a particularly advantageous combination with the gray electrochromic medium of the present invention. The combination of a bright nearly achromatic reflector, a gray electrochromic medium and a color neutral transparent conductive coating provides, for the first time, a rearview mirror which is perceived as neutral gray throughout all of its reflectance range, including intermediate reflectances.

For electrochromic mirrors the reflector may be placed on the fourth surface, in which case a layer of a transparent conductive electrode is disposed on the third surface 114a, or the reflector may be placed on the third surface 114a in accordance with the disclosure of U.S. Patent Application entitled "ELECTROCHROMIC REARVIEW MIRROR INCORPORATING A THIRD SURFACE METAL REFLECTOR" filed on or about Apr. 2, 1997. The entire disclosure of this commonly assigned co-pending U.S. Patent Application is hereby incorporated herein by reference. In this case the third surface reflector doubles as an electrode and the transparent conductive layer on the third surface is not necessary. A heater (not shown) may be placed directly on the fourth surface 114b.

The coating 120 of the third surface 114a (whether a transparent conductor or a reflector/electrode) is sealably bonded to the coating 116 on the second surface 112b near the outer perimeter by a sealing member 118, thereby defining a chamber 122. For electrochromic mirrors, sealing member 118 preferably contains glass beads (not shown) to hold transparent elements 112 and 114 in a parallel and spaced-apart relationship. Sealing member 118 may be any material which is capable of adhesively bonding the coatings on the second surface 112b to the coatings on the third surface 114a to seal the perimeter such that electrochromic medium 124 does not leak from chamber 122. Optionally, the layer of transparent conductive coating 116 and the layer on the third surface 120 (transparent conductive material or reflector/electrode) may be removed over a portion where sealing member 118 is disposed (not the entire portion, otherwise the drive potential could not be applied to the two coatings). In such a case, sealing member 118 must bond well to glass.

The performance requirements for a perimeter seal member 118 used in an electrochromic device are similar to those for a perimeter seal used in a liquid crystal device (LCD) which are well known in the art. The seal must have good adhesion to glass, metals and metal oxides, must have low permeabilities for oxygen, moisture vapor and other detrimental vapors and gases, and must not interact with or poison the electrochromic or liquid crystal material it is meant to contain and protect. The perimeter seal can be applied by means commonly used in the LCD industry such as by silk-screening or dispensing. Totally hermetic seals such as those made with glass frit or solder glass can be used, but the high temperatures involved in processing (usually near 450-degrees Centigrade) this type of seal can cause numerous problems such as glass substrate warpage, changes in the properties of transparent conductive electrode and oxidation or degradation of the reflector. Because of their lower processing temperatures, thermoplastic, thermosetting or UV curing organic sealing resins are preferred. Such organic resin sealing systems for LCD's are described in U.S. Pat. Nos. 4,297,401, 4,418,102, 4,695,490, 5,596,023 and 5,596,024. Because of their excellent adhesion to glass, low oxygen permeability and good solvent resistance, epoxy based organic sealing resins are preferred. These epoxy resin seals may be UV curing, such as described in U.S. Pat. No. 4,297,401, or thermally curing, such as with mixtures of liquid epoxy resin with liquid polyamide resin or dicyandiamide, or they can be homopolymerized. The epoxy resin may contain fillers or thickeners to reduce flow and shrinkage such as fumed silica, silica, mica, clay, calcium carbonate, alumina, etc., and/or pigments to add color. Fillers pretreated with hydrophobic or silane surface treatments are preferred. Cured resin crosslink density can be controlled by use of mixtures of mono-functional, di-functional and multi-functional epoxy resins and curing agents. Additives such as silanes or titanates can be used to improve the seal's hydrolytic stability, and spacers such as glass beads or rods can be used to control final seal thickness and substrate spacing. Suitable epoxy resins for use in a perimeter seal member 118 include but are not limited to: "EPON RESIN" 813, 825, 826, 828, 830, 834, 862, 1001F, 1002F, 2012, DPS-155, 164, 1031, 1074, 58005, 58006, 58034, 58901, 871, 872 and DPL-862 available from Shell Chemical Co., Houston, Tex.; "ARALITE" GY 6010, GY 6020, CY 9579, GT 7071, XU 248, EPN 1139, EPN 1138, PY 307, ECN 1235, ECN 1273, ECN 1280, MT 0163, MY 720, MY 0500, MY 0510 and PT 810 available from Ciba Geigy, Hawthorne, N.Y.; "D.E.R." 331, 317, 361, 383, 661, 662, 667, 732, 736, "D.E.N." 431, 438, 439 and 444 available from Dow Chemical Co., Midland, Mich. Suitable epoxy curing agents include V-15, V-25 and V-40 polyamides from Shell Chemical Co.; "AJICURE" PN-23, PN-34 and VDH available from Ajinomoto Co., Tokyo, Japan; "CUREZOL" AMZ, 2MZ, 2E4MZ, C11Z, C17Z, 2PZ, 21Z and 2P4MZ available from Shikoku Fine Chemicals, Tokyo, Japan; "ERISYS" DDA or DDA accelerated with U-405, 24EMI, U-410 and U-415 available from CVC Specialty Chemicals, Maple Shade, N.J.; "AMICURE" PACM, 352, CG, CG-325 and CG-1200 available from Air Products, Allentown, Pa. Suitable fillers include fumed silica such as "CAB-O-SIL" L-90, LM-130, LM-5, PTG, M-5, MS-7, MS-55, TS-720, HS-5, EH-5 available from Cabot Corporation, Tuscola, Ill.; "AEROSIL" R972, R974, R805, R812, R812 S, R202, US204 and US206 available from Degussa, Akron, Ohio. Suitable clay fillers include BUCA, CATALPO, ASP NC, SATINTONE 5, SATINTONE SP-33, TRANSLINK 37, TRANSLINK 77, TRANSLINK 445, TRANSLINK 555 available from Engelhard Corporation, Edison, N.J. Suitable silica fillers are SILCRON G-130, G-300, G-100-T and G-100 available from SCM Chemicals, Baltimore, Md. Suitable silane coupling agents to improve the seal's hydrolytic stability are Z-6020, Z-6030, Z-6032, Z-6040, Z-6075 and Z-6076 available from Dow Corning Corporation, Midland, Mich. Suitable precision glass microbead spacers are available in an assortment of sizes from Duke Scientific, Palo Alto, Calif.

In discussing colors it is useful to refer to the Commission Internationale de l'Eclairage's (CIE) 1976 CIELAB Chromaticity Diagram (commonly referred to as the L*a*b* chart). The technology of color is relatively complex, but a fairly comprehensive discussion is given by F. W. Billmeyer and M. Saltzman in *Principles of Color Technology*, $2^{nd}$ Edition, J. Wiley and Sons Inc. (1981), and the present disclosure, as it relates to color technology and terminology, generally follows that discussion. On the L*a*b* chart, L* defines lightness, a* denotes the red/green value and b* denotes the yellow/blue value. Each of the electrochromic media has an absorption spectra at each particular voltage that may be converted to a three number designation, their L*a*b* values. To calculate a set of color coordinates, such as L*a*b* values, from the spectral transmission or reflectance, two additional items are required. One is the spectral power distribution of the source or illuminant. The present disclosure uses CIE Standard Illuminant A to simulate light from automobile headlamps and uses CIE Standard Illuminant $D_{65}$ to simulate daylight. The second item needed is the spectral response of the observer. The present disclosure uses the 2 degree CIE standard observer. The illuminant/observer combination generally used for mirrors is then represented as A/2 degree and the combination generally used for windows is represented as $D_{65}/2$ degree.

In accordance with the present invention, the electrochromic device includes an electrochromic medium that comprises at least three electroactive materials having absorption spectra when electrochemically activated that add together such that the color of the electrochromic medium can be pre-selected by individually choosing the concentrations of the at least three electroactive materials. The at least three electroactive materials include at least one reducible material (cathodic material), at least one oxidizable material (anodic material) and at least one additional electroactive material which may be either an anodic or cathodic material. Thus, there are always three electroactive materials present in the medium, with at least two either being anodic or cathodic materials. Generally, all three electroactive materials are electrochromic such that there is a change in the absorption coefficient at at least one wavelength in the visible spectrum when electrochemically activated. However, there are instances where it is desirable to have at least two electrochromic anodic materials combined with at least one generally colorless electroactive cathodic material or, alternatively, at least two electrochromic cathodic materials combined with at least one generally colorless electroactive anodic material. In any case, at least two of the electroactive materials must be electrochromic. Finally, if the at least three electroactive compounds in their non-activated, zero-potential, equilibrium states in the solution are not ionic, the electrochromic medium further includes an electrolyte, although it should be understood that an additional electrolyte may be included when one or more of the electroactive compounds is ionic.

The electrochromic medium includes electroactive cathodic and anodic materials that may be independently chosen from at least the following three categories:

(i) Solution-Phase—a material contained in solution in the ionically conducting electrolyte which remains in solution in the electrolyte when electrochemically reduced or oxidized. Solution phase electroactive materials may be contained in the continuous solution phase of a free-standing gel in accordance with the teachings in U.S. patent application Ser. No. 08/616,967, entitled "IMPROVED ELECTROCHROMIC LAYER AND DEVICES COMPRISING SAME";

(ii) Surface-Confined—a material attached directly to an electronically conducting electrode or confined in close proximity thereto which remains attached or confined when electrochemically reduced or oxidized; and (iii) Electrodeposition—a material contained in solution in the ionically conducting electrolyte which forms a layer on the electronically conducting electrode when electrochemically reduced or oxidized.

In addition, the electrochromic medium may also include other materials like solvents, light absorbers, light stabilizers, thermal stabilizers, antioxidants, thickeners or viscosity modifiers and a free standing gel (which includes a polymer matrix).

The absorption spectra of the electrochromic materials when electrochemically activated must add together such that the color of the electrochromic medium can be pre-selected by individually choosing the concentrations or layer thickness of the electrochromic materials. In a stable device, every electron that is removed through oxidation of an anodic material must be balanced by one electron that is accepted through reduction of a cathodic material. Thus in an electrochromic medium containing three or more electroactive materials, the total number of anodic species that are oxidized must equal the total number of cathodic species that are reduced. This limitation is an important aspect in ensuring the ability to make a pre-selected color in accordance with the present invention. To illustrate this point, it is well known that one may add blue to yellow to make green, however, if an anodic material with a change from colorless to dark blue on oxidation, and a cathodic material with a change from colorless to light yellow on reduction, are added together they will always produce an electrochromic medium with the same hue throughout it normal voltage range regardless of the ratios of the concentrations of the anodic and cathodic materials. This is because the total amount of anodic material oxidized must be equal to the total amount of cathodic material reduced. Thus, even if the amount of the cathodic material that turns yellow on reduction is doubled or even tripled the color will be the same because for every cathodic species that turns yellow, one anodic species will turn blue. However, in order for the concentration of both the cathodic electroactive materials and the anodic electroactive materials to be current limiting in solution-phase systems, the total concentration of one type may be different from the total concentration of the other type due to differences in diffusion coefficients in the electrochromic medium. Often the material(s) with smaller diffusion coefficients are present at slightly higher concentrations.

In order for an electrochromic medium containing multiple electroactive anodic and cathodic materials to be able to make a pre-selected color, and generally maintain the pre-selected perceived color during darkening and clearing transitions while simultaneously being desirable for commercial applications, the medium should be photochemically and thermally stable, and all of the anodic materials present in the electrochromic medium should have similar redox potentials to each other and all of the cathodic materials present in the electrochromic medium should have similar redox potentials to each other.

If the perceived color of the device is to be consistent throughout the operation of the electrochromic device (i.e., at various applied voltages and during coloring and clearing transitions) the redox potentials of all of the cathodic materials electrochemically activated during normal operation must be similar to each other, preferably within 60 mV of each other, and the redox potentials of all the anodic materials electrochemically activated during operation must be similar to each other, preferably within 60 mV of each other. More preferably, the redox potentials of all of the cathodic materials are within 40 mV of each other and the redox potentials of all of the anodic materials are within 40 mV of each other.

Even if the redox potentials of the color-contributing cathodic materials are not similar to one another, or the redox potentials of the color-contributing anodic materials are not similar to each other, a device containing such an electrochromic medium may still exhibit a single color due to a combination of all the colors of the cathodic materials or all the colors of the anodic materials at an applied voltage high enough to reduce all of the cathodic materials arriving at the cathode and oxidize all of the anodic materials arriving at the anode. However, at lower applied voltages or during coloring transitions or especially during clearing transitions, the colors due to the most easily reduced cathodic material, i.e., those with the highest redox potentials, and/or the most easily oxidized anodic materials, i.e., those with the lowest redox potentials will dominate the perceived color of the electrochromic medium. This phenomenon is commonly referred to as staging. If the redox potentials are similar to each other (and assuming the kinetics of the electrode reactions are at least somewhat similar and that the electrochromic materials have one color which only varies in perceived chroma throughout the voltage range of the device) then the color due to the electrochromic medium will be a consistent composite of all of the color contributing cathodic and anodic materials throughout the operation of the device at various applied voltages and during coloring and clearing transitions. Stated another way, the absorption spectra of the individual cathodic materials will add together and the absorption spectra of the individual anodic materials will add together, such that the resulting absorption spectra of the electrochromic medium will produce a consistent perceived color or hue throughout the operation of the device.

Electrochromic devices should preferably be photochemically stable. Devices used in applications like rearview mirrors, especially on the exterior of motor vehicles, must have means that prevent harmful photons from reaching the electrochromic medium or must have an electrochromic medium that is stable with respect to photochemical degradation, at least for sunlight exposure over the useful life of the device while the device is in the nominally clear state. For electrochromic devices used in applications like motor vehicle or architectural windows or glazing, the device must prevent harmful photons from reaching the electrochromic medium or must have an electrochromic medium that is stable with respect to photochemical degradation both in the nominally clear state and during electrochemical activation. For electrochromic devices and media which contain multiple cathodic electrochromic materials and/or multiple anodic electrochromic materials, photons harmful to any one of the electrochromic materials must be prevented from reaching that material, or each material and the medium as a whole must be stable with respect to photochemical degradation.

Finally, the electrochromic medium should preferably be thermally stable or be such that the medium doesn't lose its ability to color or become permanently discolored due to thermal degradation. Many electrochromic media proposed in the art suffer from lack of thermal stability for one or more electrochromic materials in their nominally clear oxidation states or especially in their colored oxidation states. Lack of thermal stability results in poor cycle life for the electrochromic device. In electrochromic media that contain multiple cathodic and/or multiple anodic materials, every electrochromic material must be thermally stable enough in each of its oxidation states present in the device, with or without applied voltage, to provide the device with adequate thermal stability for its intended use and life, or the thermal degradation of these materials must not discolor the device or impede the proper operation of the device.

As stated above, the electrochromic media of the present invention comprises at least three electroactive materials having absorption spectra in their activated state that add together such that a pre-selected color of the electrochromic medium can be made by individually choosing the concentrations, relative concentrations or layer thickness of the at least three electroactive materials contained in the medium. This pre-selected color may be a wide range of perceived colors, such as red, orange, yellow, green, blue, gray, etc.

Tables 1 through 9 list a number of cathodic electrochromic materials and a number of anodic electrochromic materials that when dissolved in the proper solvent or solvent system, including enough dissolved electrolyte to provide ionic conductivity to the solution, can be used as solution-phase electrochromic materials. The solvents used are generally the polar, aprotic organic solvents taught in U.S. Pat. No. 4,902,108. In a number of these solvents, the materials in Tables 1 through 9 exhibit two chemically reversible waves in a cyclic voltammogram run at an inert electrode at room temperature. The first cyclic voltammogram wave generally is due to a one electron per molecule reduction or one electron per molecule oxidation which is accompanied by a change from colorless or slightly colored to significantly colored (i.e. light absorbing at at least one wavelength in the visible spectrum). The use of these materials in electrochromic devices is normally restricted to the electrochemical activation of the materials to this one electron reduced state or one electron oxidized state. These reduced states for cathodic materials or oxidized states for anodic materials have a particular light absorption spectrum that generally follow Beer's law throughout their range of concentrations in activated electrochromic devices, with the exception of some materials which at higher concentrations of the reduced state show complication in the spectrum due to what is believed to be dimerization.

As long as the voltage applied to an electrochromic device containing these materials is restricted to the normal range in which only the one electron reduced state or one electron oxidized state is produced at the electrodes, the materials will make a consistent color contribution varying only in the amount of absorption. If the voltage is too large, the color or visible light absorption spectrum of the twice reduced state (s) and/or twice oxidized state(s) will contribute to the overall spectrum of the electrochromic medium and therefore the electrochromic device. Going outside the normal voltage range may and often will result in a perceived change in color of the medium. For several of the materials in Tables 1 and 2, the difference in redox potential for the first one electron reduction and the second one electron reduction is quite small and therefore the normal voltage range for a device containing these materials is quite limited. Generally if an electrochromic medium contains both anodic and cathodic electrochromic materials from Tables 1 through 9, then the normal voltage across the medium is from about 0.3 volts less than the difference in redox potentials between the cathodic materials and the anodic materials to about 0.2 to 0.4 volts more than the difference in these redox potentials.

The redox potentials in Tables 1 through 9 were determined by differential pulse voltammetry at a platinum working electrode in an argon-purged propylene carbonate solution containing 0.2 molar tetraethylammonium tetrafluoroborate with an internal reference compound of known redox potential. Ultimately, all of the redox potentials in Tables 1 through 9 are given relative to the redox potential of 5,10-dimethyl-5,10-dihydrophenazine being set to 0.300 volts.

Tables 1 through 4 list four groups of cathodic electrochromic materials which change from colorless or slightly colored to significantly colored when electrochemically reduced. The tables also give the redox potentials for the first one electron reduction of each material and the wavelengths of maximum absorbance and the logarithms of the absorption coefficients at these wavelengths for the one electron reduced state of nearly all of the cathodic materials listed. Tables 5 and 6 list two more groups of cathodic electrochromic materials and the redox potentials for the first one electron reduction for each material. The redox potential for electrochemical reduction is similar within each table or group.

All of the cathodic materials in Table 1 have their redox potentials between −0.112 volts and −0.132 volts, however the one electron reduced materials have different absorption spectra with different wavelengths of maximum absorbance, which results in different perceived colors, when the materials are reduced. For example, in Table 1 materials 1 and 4 appear green in color when reduced and materials 2 and 5 appear blue in color when reduced. By choosing various relative concentrations of, for instance, materials 1 and 2, the cathodic materials' contribution to the color of the electrochromic medium can range between blue, blue-green and green.

All of the cathodic materials in Table 2 have their redox potentials between −0.192 volts and −0.216 volts. However, the spectral absorbances of the materials in their reduced states show that the materials appear different in color from each other and they can be combined in various relative concentrations to impart a particular color contribution, (different from any of the materials individually), to an electrochromic medium containing this cathodic material combination.

All of the cathodic materials in Table 3 have their redox potentials between −0.276 volts and −0.304 volts, however there are differences in their absorption spectra that lead to useful combinations of these cathodic materials in electrochromic devices.

The cathodic materials in Table 4 have redox potentials similar to each other and are between −0.340 volts and −0.376 volts. While materials 1, 3 and 5 have at least somewhat similar spectra and similar blue appearance in their reduced states, materials 2 and 4 have significantly different spectra and color appearance. When reduced, material 2 appears purple and material 4 appears green. This allows for particularly advantageous combinations for materials in Table 4 especially with regard to achieving gray color in an electrochromic mirror or window.

The cathodic materials in Table 5 have redox potentials between −0.424 and −0.436. Although the absorption coefficients have not been measured, the compounds have different absorption spectra when electrochemically reduced and can be combined with each other and/or anodic materials to give useful color contributions to the appearance of electrochromic devices.

The cathodic materials in Table 6 have redox potentials between −0.472 and −0.492. Although the absorption coefficients have not been measured the compounds have different absorption spectra when electrochemically reduced and can be combined with each other and/or anodic materials to give useful color contributions to the appearance of electrochromic devices.

TABLE 1

| | E½ | Cation Radical λ max (log ε) |
|---|---|---|
| 1. 1,1'-diphenyl-4,4'-dipyridinium bis(tetrafluoroborate) | −0.100 | 434 (4.57) 644 (4.31) 710 (4.22) |
| 2. 1,1'-bis(2,6-dimethylphenyl)-4,4'-dipyridinium bis(tetrafluoroborate) | −0.112 | 400 (4.64) 600 (4.30) 712 (3.84) |
| 3. 1,1'-bis(3,5-dimethylphenyl)-4,4'-dipyridinium bis(tetrafluoroborate) | −0.116 | 428 (4.54) 572 (4.20) 642 (4.08) 710 (3.91) |
| 4. 1-phenyl-1'-(4-dodecylphenyl)-4,4'-dipyridinium bis(hexafluorophosphate) | −0.116 | 436 (4.50) 608 (4.18) 644 (4.23) 710 (4.13) |
| 5. 1,1'-bis(2,4,6-trimethylphenyl)-4,4'-dipyridinium bis(tetrafluoroborate) | −0.116 | 400 (4.63) 600 (4.33) 712 (3.86) |
| 6. 1-(4-cyanophenyl)-1'-methyl-4,4'-dipyridinium bis(hexafluorophosphate) | −0.132 | |

TABLE 2

| | E½ | Cation Radical λ max (log ε) |
|---|---|---|
| 1. 1-(3,5-dimethoxyphenyl)-1'-methyl 4,4'-dipyridinium bis(hexafluorophosphate) | −0.192 | 410 (3.75) 606 (4.16) 710 (3.75) |
| 2. 1-methyl-1'-phenyl-4,4'-dipyridinium bis(hexafluorophosphate) | −0.204 | 414 (4.36) 608 (3.87) 712 (3.45) |
| 3. 1-methyl-1'-(2-methylphenyl)-4,4'-dipyridinium bis(hexafluorophosphate) | −0.216 | 398 (4.55) 602 (4.21) 718 (3.62) |
| 4. 1-(4-methoxyphenyl)-1'-methyl-4,4'-dipyridinium bis(hexafluorophosphate) | −0.216 | 428 (4.35) 610 (4.20) 720 (3.74) |
| 5. 1-methyl-1'-(2,4,6-trimethylphenyl)-4,4'-dipyridinium bis(hexafluorophosphate) | −0.216 | 398 (4.56) 602 (4.19) 722 (3.55) |

TABLE 3

| | E½ | Cation Radical λ max (log ε) |
|---|---|---|
| 1. 1,2,6-trimethyl-1'-phenyl-4,4'-dipyridinium bis(tetrafluoroborate) | −0.276 | 410 (4.35) 604 (4.14) |
| 2. 1,1'-dimethyl-2,6-diphenyl-4,4'-dipyridinium bis(tetrafluoroborate) | −0.292 | 400 (4.47) 636 (4.19) |
| 3. 1,1'-bis(3-phenyl(n-propyl))-4,4'-dipyridinium bis(tetrafluoroborate) | −0.296 | 398 (4.61) 604 (4.16) 732 (3.50) |
| 4. 1,1'-dimethyl-4,4'-dipyridinium bis(tetrafluoroborate) | −0.304 | 394 (4.56) 604 (4.12) 738 (3.50) |

TABLE 4

| | E½ | Cation Radical λ max (log ε) |
|---|---|---|
| 1. 1,1'-dimethyl-2-(3-phenyl(n-propyl))-4,4'-dipyridinium bis(hexafluorophosphate) | −0.340 | 396 (4.57) 608 (4.18) 730 (3.47) |
| 2. 1,1'-dimethyl-4,4'-(1,3,5-triazine-2,4-diyl)dipyridinium diperchlorate | −0.352 | 556 (3.86) |
| 3. 1,1'-dibenzyl-2,2',6,6'-tetramethyl-4,4'-dipyridinium bis(tetrafluoroborate) | −0.360 | 396 (4.49) 590 (4.22) 688 (3.83) |
| 4. 1,1'-ethylene-4,4'-dimethyl-2,2'-dipyridinium bis(hexafluorophosphate)* | −0.360 | 432 (3.81) 468 (3.85) 748 (3.53) |
| 5. 1,1'-dimethyl-2,2'-bis(3-phenyl(n-propyl))-4,4'-dipyridinium bis(tetrafluoroborate) | −0.376 | 396 (4.60) 610 (4.25) 725 (3.61) |

*IUPAC name: 6,7-dihydrodipyrido-[1,2-a:1'-c]pyrazinediium bis(hexafluorophosphate)

TABLE 5

| | E½ |
|---|---|
| 1. 1,6-diethyl-1,6-diazapyrene-2,5,7,10-tetraketone | −0.424 |
| 2. 1,1',2,2',3,3',4,4'-octahydro-8,8'-biquinolizinium bis(tetrafluoroborate) | −0.436 |
| 3. 1,1',2-trimethyl-2',6,6'-tris(2-phenylethyl)-4,4'-dipyridinium bis(tetrafluoroborate) | −0.436 |

TABLE 6

| | E½ |
|---|---|
| 1. 2,6-dimethylbenzoquinone | −0.472 |
| 2. 1,4-dihydroxyanthraquinone | −0.472 |
| 3. 1-methyl-4-(1,3,5-triazine-2-yl)-pyridinium hexafluorophosphate | −0.472 |
| 4. 1,1',2,2',6-pentamethyl-6'-n-hexyl-4,4'-dipyridinium bis(hexafluorophosphate) | −0.484 |
| 5. 1,1',2,2'-tetramethyl-6,6'-bis-n-hexyl-4,4'-dipyridinium bis(hexafluorophosphate) | −0.488 |
| 6. 1,1',2,2',6-pentamethyl-6'-(3-phenyl(n-propyl))-dipyridinium bis(hexafluorophosphate) | −0.492 |

Tables 7 through 9 list groups of anodic materials that are colorless or slightly colored which change to significantly colored when electrochemically oxidized. The tables also give the redox potentials for the first one electron oxidation of each material and the wavelengths of maximum absorbance and the logarithms of the absorption coefficients at these wavelengths for the one electron oxidized state of the anodic materials listed.

All of the anodic materials in Table 7 have their redox potentials between 0.256 volts and 0.264 volts, however the one electron oxidized materials all have different absorption spectra. The oxidized materials appear blue, brown, purple or green and can be combined in selected relative concentrations in electrochromic devices to impart any of a number of particular or predetermined color contributions.

All of the anodic materials in Table 8 have their redox potentials between 0.290 volts and 0.308 volts. The wavelength of maximum absorbance for the main absorbance peak of the oxidized state of these materials varies from 460 nanometers to 532 nanometers. Numerous useful combinations of these materials at selected relative concentrations can be used in electrochromic devices to achieve a particular color appearance contribution.

Finally, all of the anodic materials in Table 9 have similar redox potential to each other and are between 0.344 volts and 0.352 volts. Even though the redox potentials are similar the color appearance and absorption spectra are different and combinations at selected relative concentrations are useful for imparting a particular color appearance to electrochromic devices.

In accordance with an important aspect of the present invention, Table 10 shows the results of combining various concentrations of a number of the materials from Tables 1 through 9 in the electrochromic medium of an electrochromic device and how the concentrations of at least three electroactive materials may be chosen to produce a device having a pre-selected perceived color. Because the anodic materials and the cathodic materials themselves are chosen such that they have similar redox potentials, the electrochromic medium maintains the predetermined perceived color in its electrochemically activated states throughout its normal range of voltages.

TABLE 7

| | $E_{1/2}$ | Cation Radical<br>λ max (log ε) |
|---|---|---|
| 1. N,N,N',N'-tetramethyl-p-phenylenediamine | 0.256 | 566 (4.11) 6.14 (4.13) |
| 2. 2,5,10-trimethyl-3-phenyl-5,10-dihydrophenazine | 0.260 | 494 (4.04) 614 (3.16) 666 (3.22) 730 (3.10) |
| 3. 5-ethyl-10-methyl-5,10-dihydrophenazine | 0.264 | 450 (3.91) 606 (3.02) 660 (3.21) 726 (3.17) |
| 4. 5,10-dimethyl-5,10-dihydrobenzo(A)phenazine | 0.264 | 532 (3.86) 670 (3.38) |

TABLE 8

| | $E_{1/2}$ | Cation Radical<br>λ max (log ε) |
|---|---|---|
| 1. 2,7-diphenoxy-5,10-dimethyl-5,10-dihydrophenazine | 0.290 | 516 (4.11) 682 (3.40) |
| 2. 2-phenoxy-5,10-dimethyl-5,10-dihydrophenazine | 0.292 | 506 (3.99) 654 (3.32) |
| 3. 2,7-bis(o-tolyl)-5,10-dimethyl-5,10-dihydrophenazine | 0.292 | 512 (4.17) 680 (3.40) 744 (3.31) |
| 4. 2,3-dimethyl-7-trifluoromethyl-5,10-diethyl-5,10-dihydrophenazine | 0.292 | 482 (4.09) 652 (3.29) 716 (3.16) |
| 5. 5,10-dimethyl-5,10-dihydrophenazine | 0.300 | 460 (3.97) 608 (3.11) 660 (3.27) 7.28 (3.21) |
| 6. 2,3-diphenyl-5,10-dimethyl-5,10-dihydrophenazine | 0.300 | 532 (4.04) 676 (3.30) 744 (3.10) |
| 7. 2,7-diphenyl-5,10-dimethyl-5,10-dihydrophenazine | 0.300 | 532 (4.13) 702 (3.52) 768 (3.50) |
| 8. 2-vinyl-5,10-dimethyl-5,10-dihydrophenazine | 0.300 | 484 (3.94) 670 (3.27) 734 (3.21) |
| 9. 2-phenyl-5,10-dimethyl-5,10-dihydrophenazine | 0.308 | 496 (4.00) 676 (3.31) 744 (3.23) |

TABLE 9

| | $E_{1/2}$ | Cation Radical<br>λ max (log ε) |
|---|---|---|
| 1. 5,10-diisopropyl-5,10-dihydrophenazine | 0.344 | 480 (3.94) 682 (3.23) 752 (3.19) |
| 2. 5,10-dimethyl-5,10-dihydrodibenzo(A,C)phenazine | 0.344 | 536 (4.02) |
| 3. 1,5,10-trimethyl-2-phenyl-5,10-dihydrophenazine | 0.348 | 496 (3.95) 714 (3.16) 772 (3.08) |
| 4. 2,3,5,10-tetramethyl-7-trifluoromethyl-5,10-dihydrophenazine | 0.348 | 482 (4.04) 658 (3.08) 714 (3.05) |
| 5. 2,3,5,10-tetramethyl-5,10-dihydrobenzo(B)phenazine | 0.352 | 436 (4.01) 534 (4.14) |

TABLE 10

| | Concentration of Anodic Material (millimolar) | | | | | | Concentration of Cathodic Materials (millimolar) | | | | | Color Coordinates of Window in Full Colored State (A/2 degree) | | | |
|---|---|---|---|---|---|---|---|---|---|---|---|---|---|---|---|
| | A1 | A2 | A3 | A4 | A5 | A6 | C1 | C2 | C3 | C4 | C5 | L* | a* | b* | Y |
| 1. | 20 | 10 | 5 | — | — | — | — | 15 | 25 | — | — | 39.93 | −1.77 | 11.26 | — |
| 2. | 15 | 7.5 | 3.8 | — | — | — | 30 | — | — | — | — | 32.84 | −5.65 | −26.22 | — |
| 3. | 17 | 8.5 | 4.3 | — | — | — | — | 17 | 17 | — | — | 40.19 | −0.88 | 3.40 | 11.37 |
| 4. | 17 | 8.5 | 4.3 | — | — | — | — | 19 | 15 | — | — | 35.39 | 0.07 | −2.39 | 8.70 |
| 5. | 15 | 15 | — | — | — | — | 30 | — | — | — | — | 30.31 | −2.72 | −24.84 | 6.36 |
| 6. | 20 | 10 | — | — | — | — | 30 | — | — | — | — | 33.36 | −10.32 | −20.06 | 7.70 |
| 7. | 28 | — | — | — | — | — | 34 | — | — | — | — | 34.34 | −28.76 | −15.79 | 8.17 |
| 8. | 15 | 10 | — | — | — | — | 30 | — | — | — | — | 34.91 | −9.20 | −23.35 | 8.45 |
| 9. | 22 | — | 6 | — | — | — | 34 | — | — | — | — | 31.71 | −11.70 | −21.86 | 6.96 |
| 10. | 24 | — | 4 | — | — | — | 34 | — | — | — | — | 32.45 | −15.19 | −18.68 | 7.29 |
| 11. | — | — | — | — | 20 | 5 | 30 | — | — | — | — | 33.41 | −18.10 | −18.00 | 7.73 |
| 12. | — | — | — | — | 20 | 5 | — | — | — | 15 | 15 | 47.43 | −8.46 | −7.44 | 16.35 |
| 13. | 20 | — | 5 | — | — | — | — | — | 3 | 6 | 21 | 37.16 | −13.37 | −16.10 | 9.63 |
| 14. | 19.2 | — | — | — | — | 4.8 | — | — | — | 14 | 14 | 48.35 | −3.13 | −9.58 | 17.07 |

See next page for designations of A1–A6 and C1–C5
A1 = 5,10-dimethyl-5,10-dihydrophenazine
A2 = 2-phenyl-5,10-dimethyl-5,10-dihydrophenazine
A3 = 2,3-diphenyl-5,10-dimethyl-5,10-dihydrophenazine
A4 = 5-ethyl-10-methyl-5,10-dihydrophenazine
A5 = 2,5,10-trimethyl-3-phenyl-5,10-dihydrophenazine
A6 = 2,7-diphenoxy-5,10-dimethyl-5,10-dihydrophenazine
C1 = 1,1'-bis(3-phenyl(n-propyl))-4,4'-dipyridinium bis(tetrafluoroborate)
C2 = 1,1'-dibenzyl-2,2',6,6'-tetramethyl-4,4'-dipyridinium bis(tetrafluoroborate)
C3 = 1,1'-ethylene-4,4'-dimethyl-2,2'-dipyridinium bis(hexafluorophosphate)
C4 = 1,1'-dimethyl-4,4'-(1,3,5-triazine-2,4-diyl)dipyridinium diperchlorate
C5 = 1,1'-dimethyl-2-(3-phenyl(n-propyl))-4,4'-dipyridinium bis(hexafluorophosphate)

The results of Table 10 are shown in terms of the L*a*b* color coordinates of transmitted light when the electrochromic window devices were in their full colored state. This is the state in which L* is a minimum, the chroma is a maximum and a* and b* are furthest from the a*=0 and b*=0 origin (for the normal operation of the device). The electrochromic devices were fabricated using parallel, planar, spaced apart sheets of glass coated on the surfaces facing each other with fluorine-doped tin oxide, (TEC 15 coated glass available from Libbey-Owens-Ford of Toledo, Ohio). The spacing between the fluorine-doped tin oxide layers (cell spacing), was 137 microns. At least one electrochromic window device was filled with a propylene carbonate solution containing each of the various millimolar (mM) concentrations and combinations of anodic material (s) and cathodic material(s) for each row of Table 10. The visible spectrum of the device in its clear state with no voltage applied was subtracted from the full colored state, normally with 0.6 to 1.0 volts applied. This difference spectra was converted to the color coordinates (Standard Illuminant A/2-degree), shown on the right hand side of the table by a standard method known in the art. Also shown is Y, the measure of brightness.

Referring specifically to Row 7, an electrochromic medium comprising an anodic and a cathodic electrochromic material is shown whose relative concentration is found in commercially available electrochromic mirrors. In an electrochromic window with this electrochromic medium in the full colored state, the color coordinates show a large negative a* or green appearance and a somewhat smaller negative b* or some blue appearance and the fully colored window appears green-blue-green. Also of particular note are the electrochromic window devices with the concentrations/combinations given in rows 3 and 4 which have very low absolute a* and b* values and which appear nearly perfectly gray and the devices of rows 12 and 14 which also have relatively small values for a* and b* and give near neutral gray appearance with various applied voltages and transmission levels including the lowest transmission level or full colored state. In Table 10, all of the anodic materials combined in one device have redox potentials similar to each other and all of the cathodic materials combined in one device have redox potentials similar to each other. Therefore the devices have the same perceived color throughout their coloration or darkening range, which is to say the devices lack staging of colors both during coloration and clearing.

It should be understood that with the data in Tables 1 through 10, not only combinations of various anodic electrochromic materials and cathodic electrochromic materials can be chosen, but various relative concentrations of each anodic material and cathodic material can be chosen. All such combinations of electrochromic materials that when combined give a gray device should be understood to be within the scope of the present invention.

FIG. 2 illustrates a method by which a predetermined color for an electrochromic medium can be chosen. The visible light absorption spectrum for the colored state or in this case the cation radical of each of the compounds listed below for FIG. 2 was determined. Each nominal spectrum was determined for the same path length and concentration for the colored state of each material and was scaled as described below. As described earlier, in a stable electrochromic device the number of electrons added to the electrochromic medium equals the number of electrons removed during electrochemical activation and, (as is this case for these materials listed below for FIG. 2), if electrochemical activation involves one electron reduction for each cathodic compound and one electron oxidation for each anodic compound the total number or effective concentration of activated cathodic species will equal the total number or effective concentration of activated anodic species.

Thus the percentages of the spectra for the cathodic species and the percentages of the spectra for the anodic species will each add up to 100%. Curve A1 shows 80% of the nominal spectrum of the cation radical of 5,10-dimethyl- 5,10-dihydrophenazine, Curve A6 shows 20% of the nominal spectrum of the cation radical of 2,7-diphenoxy-5,10-dimethyl-5,10-dihydrophenazine, Curve C4 shows 50% of the nominal spectrum of the cation radical of 1,1'-dimethyl-4,4'-(1,3,5-triazine-2,4-diyl)dipyridinium diperchlorate, and Curve C5 shows 50% of the nominal spectrum of the cation radical of 1,1'-dimethyl-2-(3-phenyl(n-propyl))-4,4'-dipyridinium bis(hexafluorophosphate). These scaled spectra were added together to give the composite spectrum that would be essentially the same as that observed in an electrochemically activated electrochromic medium containing these relative concentrations of these electrochromic compounds.

The absorbances in FIG. 2 are shown on a relative scale as the absorbance of the electrochromic medium, once activated, will have the same shape (or relative peak heights and peak positions), shown but will increase as a whole as the voltage is increased. As described above, the absorbance spectrum shape will remain the same throughout the normal voltage range of the electrochromic medium which is generally from about 0.3 volts less than the difference in redox potentials between the anodic materials and the cathodic materials to about 0.2 to 0.4 volts more than the difference in these redox potentials. In this case, the normal operating voltage range across the medium for the materials in FIG. 2 would be from about 0.35 volts to about 0.95 volts since the anodic materials have redox potentials around +0.300 volts and the cathodic materials have redox potentials around –0.350 volts for a difference of 0.650 volts. Throughout this voltage range and different levels of darkening, an electrochromic window containing an electrochromic medium comprised of the electrochromic materials in FIG. 2 in the given relative concentration ratios will maintain a constant blue-gray appearance. The device could be said to maintain nearly constant hue as its magnitude of chroma is increased.

FIG. 3 shows the scaled spectra of: the cation radical of 5,10-dimethyl-5,10-dihydrophenazine in Curve A; the cation radical of 2,3-diphenyl-5,10-dimethyl-5,10-dihydrophenazine in Curve B; a tungsten trioxide film which has been electrochemically reduced in the presence of lithium ion to form $Li_xWO_3$ in Curve C. The sum or composite spectrum for the scaled spectra of these three electrochromic materials is shown in Curve D. An electrochromic device containing this electrochromic medium has a surface confined $WO_3$ layer on one electrode (either the second or third surface) and a solution of propylene carbonate containing the two anodic materials and a lithium salt (e.g., $LiClO_4$, to provide ionic conductivity and a lithium ion source), in contact with the other electrode and the $W_3$ layer. The spectra are scaled such that 60% of the anodic material to be electrochemically activated is 5,10-dimethyl-5,10-dihydrophenazine and 40% is 2,3-diphenyl-5,10-dimethyl-5,10-dihydrophenazine, and the tungsten trioxide film thickness is chosen to allow the absorbance in its reduced state to have the spectral contribution relative to the anodic materials shown in FIG. 2.

The electrochromic device is still self-erasing, like an all solution-phase device, since the oxidized anodic materials can diffuse to the reduced tungsten trioxide film and spontaneously exchange electrons to oxidize the reduced film and reduce the oxidized anodic materials. Thus the fully colored device would spontaneously return to its clear condition even at open circuit.

The relative and total concentrations of these anodic materials which have similar redox potentials and the thickness of tungsten trioxide layer can be chosen to give a gray appearing electrochromic device as is illustrated by the spectrum in Curve D. For this composite spectrum scaled to an L* value of 53.72, a moderate amount of coloration, the following color coordinates are obtained: a*=2.18 and the b*=–3.24 (for $D_{65}/2$ degree). This is a remarkable achievement for tungsten trioxide based devices which usually suffer from being pure blue in appearance at moderate coloration when the electrochromic medium includes tungsten trioxide as an electrochromic material.

Likewise, the anodic material can be in the form of a surface-confined layer, such as a metal oxide (including $M_xV_2O_5$, $NiO_xH_y$, $M_xCeO_2$, $M_xNb_2O_5$, $IrO_x$, along with Ce/Ti, Zr/Ce, and W/Ce mixed oxides). An electrochromic device containing this electrochromic medium has the surface-confined layer on the second or third surface and a solution of the two or more cathodic materials, e.g., viologens, in a suitable solvent. The solution also contains a soluble ionic material (typically a lithium salt) in order to support ionic conductivity and to provide an ion source for intercalation of the surface-confined layer. The relative and total concentrations of the cathodic materials and the thickness of the surface-confined anodic layer can be chosen to give a pre-selected perceived color, including gray.

For an electrochromic medium containing an electrodeposition type electrochromic material which is cathodic, two or more solution-phase anodic materials of similar redox potential can be combined in the medium in relative concentrations to produce a pre-selected perceived color appearance, including gray. The pre-selected relative concentrations of the anodic materials can be chosen based on the absorption spectra of the electrodeposited film, those of the anodic materials and the rate of the self-erasing reaction. For an anodic electrodeposition type electrochromic material, two or more cathodic materials with similar redox potentials can be combined in the electrochromic medium as described above to produce a pre-selected perceived color appearance, including gray.

In general, the absorption spectra of the electrochemically activated states of electrochromic materials can be scaled and summed in the fashion discussed above to choose materials and relative concentrations that will give an electrochromic medium with a particular (and pre-selected) perceived color throughout their normal operating voltage ranges. While the invention has been illustrated using several types of electroactive and electrochromic materials, being able to pre-select the perceived color is broad and applicable to electrochromic media comprised of organic, inorganic, organometallic, and polymeric materials, which may be solution-phase, electrodeposition and surface confined electroactive and electrochromic materials, as well as combinations thereof.

In certain applications, such as architectural windows and motor vehicle mirrors, the pre-selected color of the electrochromic medium may be one that is perceived as gray. In the broadest terms, a color that is perceived as gray is an achromatic color of lightness between black and white and, although achromatic is defined as a color perceived to have zero saturation and therefore no hue, it should be construed broader in the context of the present invention to mean a color perceived to have a little or moderate amount of chroma. Although the meaning of chroma will be understood to those skilled in the art, it may be helpful to refer to the L*a*b* chart. As stated above, on the L*a*b* chart, L* defines lightness, a* denotes the red/green value and b* denotes the yellow/blue value. According to the present invention and further described in the following paragraphs, a little or moderate amount of saturation is defined as a color around (and including) a*=0 and b*=0 that is perceived as gray when viewed by human eyesight under particular conditions. In the narrowest sense, the gray color can be defined by a circle around $a^*=0$ and $b^*=0$ having a radius $C^*$ where $C^*=(a^{*2}+b^{*2})^{1/2}$.

Figure 4:
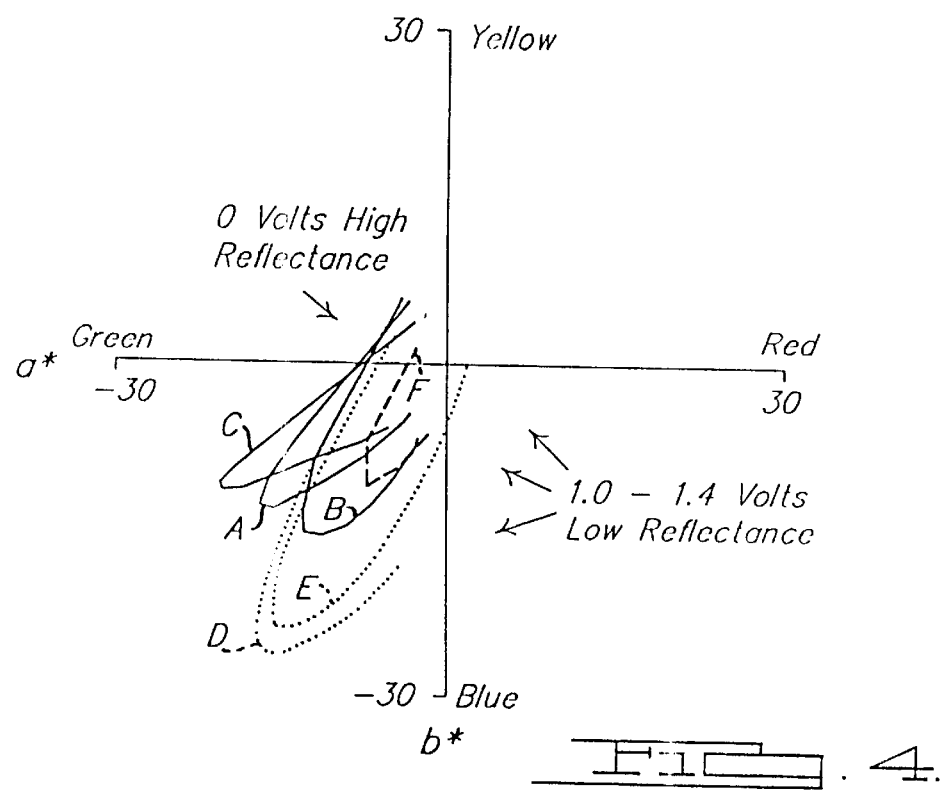
FIG. 4 shows several curves representing the color coordinates of various electrochromic mirrors incorporating various electrochromic media as the mirrors are transitioned from their clear or high reflectance states to their dark or low reflectance states.

FIG. 4 shows excursions in $a^*b^*$ color coordinate space (A/2 degree) for a number of electrochromic mirrors suitable for use as rearview mirrors in motor vehicles.

The excursions in color coordinate space for windows are generally very helpful for choosing electrochromic media for use in mirrors and visa versa, however, in contrast to the curves in FIG. 5 (discussed below) which are nearly linear, the curves in FIG. 4 have a definite semi-elliptical shape. The reason for this is believed to be as follows: the starting color coordinates for a mirror in its high reflectance state are determined largely by the color imparted to the light by two passes through the glass substrate(s), transparent electrode (s) and the non-activated electrochromic medium (each of which may have some slight absorption of light at some visible wavelengths), and the slight non-uniform reflectance (with respect to light of visible wavelengths), due to the transparent electrode(s) and the mirror reflector layer(s). Thus electrochromic mirrors often appear slightly yellow or yellowish-green in their high reflectance state and the color coordinates for all of the mirrors shown in FIG. 4 are in the green-yellow ($-a^*$, $+b^*$) quadrant in the high reflectance, zero-applied voltage state.

As the mirrors begin to dim by applying a voltage to, and thereby decreasing the transmission level of, the electrochromic medium, the color coordinates of the reflected light become largely determined by the color or visible light absorption spectra of the electrochromic medium. This is shown in FIG. 4 by the excursion of the color coordinates into the green-blue ($-a^*$, $-b^*$) quadrant as the applied voltage is increased. As the mirror continues to dim, the amount of light not absorbed by two passes through the electrochromic device, (including the electrochromic medium), starts to become comparable to the residual and secondary reflections due to the first surface of the front glass substrate, the interface between the front glass substrate and the transparent electrode layer and the interface between the transparent electrode layer and the electrochromic medium.

In general, these residual and secondary reflections are relatively colorless if the transparent electrode layer(s) provide for color suppression of the transparent electrode structure, (as is the case for TEC 15 glass available from LOF of Toledo, Ohio, or the color neutral coatings disclosed in commonly assigned co-filed U.S. Patent Application entitled "AN ELECTROCHROMIC MIRROR WITH TWO THIN GLASS ELEMENTS AND A GELLED ELECTROCHROMIC MEDIUM, the entire disclosure of which is hereby incorporated herein by reference). Therefore in this reflectance region the color coordinates of the reflected light start to become less dominated by the color or visible light absorption spectra of the electrochromic medium and start to become dominated by the relatively colorless residual and secondary reflections and the curves in FIG. 4 start to "turn around". As the reflectance continues to decrease, the color coordinates of the reflected light become largely dominated by the color of the residual and secondary reflections and often head toward relatively small absolute values of $a^*$ and $b^*$. Thus, at the highest applied voltage or lowest reflectance levels, the color coordinates for the mirrors in FIG. 4 (with the exception of Curve E) are still in the green-blue quadrant but are closer to the $a^*$, $b^*$ equal 0, 0 than at intermediate reflectance levels.

The desirability of an electrochromic mirror for use as a motor vehicle rearview mirror, with regard to color, depends on the perceived color of the clear, high reflectance state; the perceived color of lowest reflectance state (often determined mostly by residual and secondary reflections); and the perceived color of the intermediate reflectance states.

As stated earlier, commercial electrochromic rearview mirrors typically have a slightly yellowish or yellowish-green tint in their high reflectance state with $L^*$ typically 90±5, $a^*$ typically of $-4\pm3$ and $b^*$ typically 5±3. Most desirable for many people would be an $L^*$ as high as possible and $a^*$ and $b^*$ each as close to zero as possible.

The actual electrochromic mirrors which were used to obtain the color coordinate curves in FIG. 4 as a function of applied voltage are described below. The mirrors with color coordinate Curves A, B and D were constructed of two flat sheets of TEC 15 glass each 2.3 mm thick bonded together with an epoxy seal which provided a 137 micron spacing with the TEC 15 tin oxide coatings provided on surfaces 2 and 3. The mirrors had a fourth surface reflector made up of a conventional silver reflector over-coated with copper and paint layers applied to the back surface of the sheet of TEC 15 glass that was the rear glass element. The mirror with color coordinate Curve F was a large outside rearview mirror (about 12 centimeters high and 20 centimeters wide) which had front and rear glass elements that were 1.1 mm thick sheets of glass bonded together with an epoxy seal which provided a 180 micron spacing between surfaces 2 and 3. On surface 2 was a color suppressed transparent electrode structure made up of about 300 Å of ITO, about 300 Å of silicon dioxide, followed by about 1500 Å of ITO and the coated glass element was essentially colorless when viewed both in transmission and reflection. On Surface 3 was a reflector electrode structure made up of a first layer of chromium metal, an intermediate layer of rhodium metal and a top layer of silver-gold alloy which contained 85% silver and 15% gold by weight. This reflector was essentially achromatic in appearance. In addition to the electrochromic materials described below, the electrochromic medium of the mirror of Curve F also contained a polymer matrix, which with the electrochromic solution, formed a free-standing gel. The free-standing gel electrochromic medium was prepared according to the teachings of commonly assigned co-pending U.S. patent application Ser. No. 08/616,967 entitled, "IMPROVED ELECTROCHROMIC LAYER AND DEVICES COMPRISING SAME" to W. L. Tonar, et al., the entire disclosure of this patent application, including the references contained therein, is hereby incorporated by reference. This mirror had a high end reflectance for CIE curve white light of 85%, a low end reflectance of 7% and an achromatic, "silver", or gray appearance at high, low and all intermediate reflectance levels.

Curve A shows the color coordinates (A/2 degree) for various reflectances states of an electrochromic mirror having an electrochromic medium comprising: 30 mM 1,1'-bis (3-phenyl(n-propyl))-4,4'-dipyridinium bis (tetrafluoroborate); 20 mM 5,10-dimethyl-5,10-dihydrophenazine; and 4 mM 2,3-diphenyl-5,10-dimethyl-5,10-dihydrophenazine. Curve A has a maximum $C^*$ of 21.56 and a maximum $a^*$ of −17.24. Curve B shows the color coordinates (A/2 degree) for various reflectances states of an electrochromic mirror having an electrochromic medium comprising: 30 mM 1.1'-bis(3-phenyl(n-propyl))-4,4'-bipyridinium bis(tetrafluoroborate); 18 mM 5,10-dimethyl-5,10-dihydrophenazine; and 7.2 mM 2,3-diphenyl-5,10-dimethyl-5,10-dihydrophenazine. Curve B has a maximum $C^*$ of 20.24 and a maximum $a^*$ of −13.15.

Curves C, E and D show color coordinates (A/2 degree) for the various reflectance states of electrochromic mirrors commercially available in Europe, the United States, and throughout the world, respectively. Curve C has a maximum C* of 28.63 and a maximum a* of −15.77, Curve D has a maximum C* of 23.53 and a maximum a* of −20.48, and Curve E has a maximum C* of 31.13 and a maximum a* of −1 6.84. The mirrors represented by Curves A and B (4 mM and 7.2 mM 2,3-diphenyl-5,10-dimethyl-5,10-dihydrophenazine, respectively), when viewed at night in a motor vehicle have a neutral gray appearance, while the devices shown in Curves C and E have blue appearances, and the device shown in Curve D has a green or green-blue appearance. This seemingly small change in C* (the difference between 21.56 and 23.53 or 28.44) represents a significant change in the perceived color of the device. Curve F shows the color coordinates (A/2 degree) for the various reflectances states of an electrochromic mirror having an electrochromic medium comprising: 12 mM 1,1'-dimethyl-2-(3-phenyl(n-propyl)) −4,4'-dipyridinium bis (hexafluorophosphate); 12 mM 1,1'-dimethyl-4,4'-(1,3,5-triazine-2,4-diyl)dipyridinium diperchlorate; 16 mM 5,10-dimethyl-5,10-dihydrophenazine (DMP); and 4 mM 2,7-diphenoxy-5,10-dimethyl-5,10-dihydrophenazine. Curve F has a maximum C* of 13.51 and a maximum a* of −7.48, and when viewed at night in a motor vehicle gives a neutral gray appearance. Thus, the difference in the perceived color of mirrors having a C* value of 21.56 and 23.53 (a 8% change) is significant, whereas the difference in the perceived color of mirrors having a C* value of 13.51 and 21.56 (a 37% change) are both perceived as gray. It seems clear that, in the narrowest sense, a color is perceived as gray for reflected headlamps when viewed during night driving in a motor vehicle when its color coordinates (A/2-degree) have a maximum C* value below about 22, especially if the a* value is between −18 and zero.

Although it is not certain, it is generally believed, that for electrochromic rearview mirrors for motor vehicles which are dimmed at night, when the driver's eyes are at least partially dark adapted, and which mirrors generally have their perceived color in the dimmed state determined by the color of reflected headlamp light, that if there is some perceived color, the most preferred or acceptable colors, whether for physiological or psychological reasons or not, are in the green-blue quadrant of the a*, b* color coordinate space. In fact, for mirror acceptance as relatively gray, there tends to be slightly more tolerance for excursions in the −b* or the blue direction than in the −a* or the green direction as long as the C* value stays below a maximum value of about 22. This is borne out in FIG. 3 in that a mirror like that of Curve D is perceived as being somewhat green in the intermediate reflectance states, (near maximum C* values) during moderate glare night driving conditions. Mirrors which have color coordinate excursions during reflectance changes like Curves A and B are perceived as being much closer to gray, even at intermediate reflectance levels, while mirrors with Curves C and E are definitely perceived as blue in their intermediate reflectance states.

It has been determined that, for motor vehicle drivers at night, the perception will be that the mirror is essentially gray throughout its reflectance range if it has a maximum C* value of less than about 22, especially if the a* value between −18 and zero. It has also been determined that Curve A is considered the limit of acceptability for a mirror perceived as gray in its intermediate reflectance states and mirrors of Curves B and F are considered to be essentially neutral or gray throughout their entire reflectance range.

Almost all commercial electrochromic rearview mirrors have most of their color coordinate excursion in the green-blue quadrant. This may not be a total coincidence since mirrors that have color coordinate excursions into the +a* (red) and −b* (blue) quadrant during their reflectance changes can appear purple which gives an eerie feeling to drivers using these mirrors during glare conditions at night. Mirrors that have color coordinate excursions into the −a* (green) and +b* (yellow) quadrant are considered undesirable by drivers and have difficulty being low enough in reflectance to relieve strong glare. This is for the same reason that a dark yellow window still has significant light transmission. There is some thought that mirrors with a color coordinate excursion into the +a* (red) and +b* (yellow) quadrant (especially with +a* values larger than the +b* values), would be desirable for some drivers who like red or orange display lighting in a motor vehicle but in general mirrors with this type of color coordinate excursion are controversial. Therefore the −a* (green) and −b* (blue) quadrant is preferred for the color coordinates of rearview mirrors in their intermediate reflectance states, especially if C* and a* are limited as described above.

Figure 5:
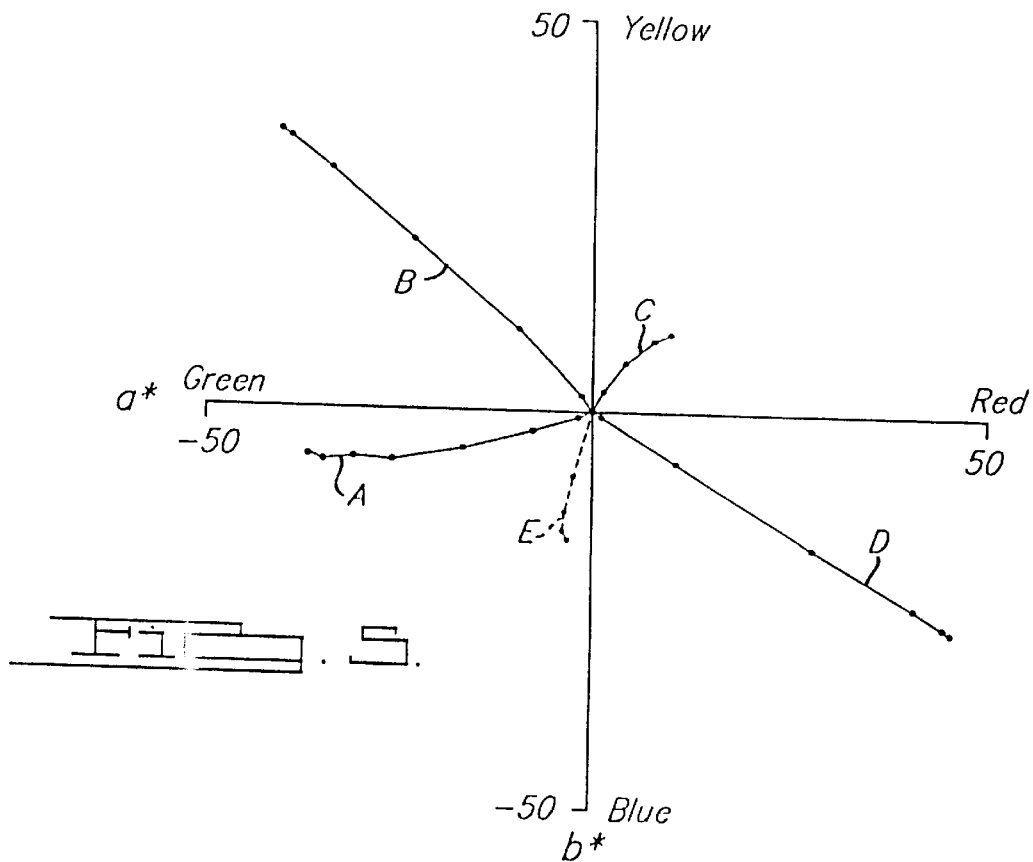
FIG. 5 shows several curves representing the color coordinates of various electrochromic media incorporated in various electrochromic windows as the windows are transitioned from their clear or high transmission states to their dark or low transmission states.

FIG. 5 shows color coordinate excursions ($D_{65}/2$ degree) for four electrochromic windows in Curves A through D (each made with TEC-15 glass with a cell spacing of 137 microns), and Curve E shows the color coordinate excursions ($D_{65}/2$ degree) for the composite spectrum of FIG. 2 multiplied by various factors to simulate various values of L* or levels of transmission. For each of the experimental electrochromic windows, the spectrum of the window at 0.0 volts is subtracted from the spectrum at each applied voltage so that the color coordinates are calculated essentially for the electrochromic medium alone.

Curve A is for an electrochromic window containing a propylene carbonate solution of 28 mM 5,10-dimethyl-5,10-dihydrophenazine and 34 mM 1,1'-bis(3-phenyl(n-propyl))-dipyridinium bis(tetrafluoroborate). As the voltage applied to the window is increased from 0.0 volts to 1.0 volts the color coordinates for light transmitted by the medium change from a L*, a*, b* of 100, 0, 0 to a fairly green slight blue appearance at a L*, a*, b* of 40.14, −36.47, −5.87. Simply using straight lines to connect the data points at various voltages results in a relatively straight line overall, and for this electrochromic medium containing only two materials the color or hue remains consistent throughout the normal voltage and transmission range of the device.

Curve B shows color coordinate data for an electrochromic medium for which it was desired to make a window with a bright green appearance. The window was filled with a propylene carbonate solution of 25 mM 5,10-dimethyl-5,10-dihydrophenazine, 10 mM 1,1'-dibenzyl-2,2',6,6'-tetramethyl-4,4'-dipyridinium bis(tetrafluoroborate) and 20 mM 1,1'-ethylene-4,4'-dimethyl-2,2'-dipyridinium bis (hexafluorophosphate). As can be seen from Curve B this electrochromic medium changes from a L*, a*, b* equal 100, 0, 0 or colorless at 0.0 volts to a L*, a*, b* equal 64.12, −40.58, 35.17 at 1.0 volts. Because the two cathodic materials have similar redox potential, even though they have significantly different absorption spectra, the medium has the same apparent bright green color or consistent hue throughout its normal voltage and transmission range.

Curve C is for an electrochromic window filled with a propylene carbonate solution of 20 mM 5,10-dimethyl-5,10-dihydrophena, 4 mM 2,3-diphenyl-5,10-dimethyl-5,10-dihydrophenazine and 30 mM 1,1 '-dimethyl-4,4'-(1,3,5-triazine-2,4-diyl)-dipyridinium bis(tetrafluoroborate). This electrochromic medium had a consistent hue with a perceived red/brown color throughout its normal voltage and transmission range which took the color coordinates for the medium from L*, a*, b* equal 100, 0, 0 at 0.0 volts to L*, a*, b* equal 53.70, 9.44, 9.70 at 1.0 volts.

Curve D shows what happens if the relative concentration of the anodic materials in Curve C are reversed. The window for Curve D was filled with a propylene carbonate solution of 4 mM 5,10-dimethyl-5,10-dihydrophenazine, 20 mM 2,3-diphenyl-5,10-dimethyl-5,10-dihydrophenazine and 30 mM 1,1'-dimethyl-4,4'-(1,3,5-triazine2,4-diyl)-dipyridinium bis(tetrafluoroborate). This medium, with its reversed relative concentrations as compared to the window of Curve C; had a consistent hue with a perceived red/magenta color throughout its normal voltage and transmission ranges which took the color coordinates from L*, a*, b* equal 100, 0, 0 at 0.0 volts to L*, a*, b* equal 43.70, 45.23, −27.19 at 1.0 volts.

Curve E shows color coordinates for the composite spectra of FIG. 2 multiplied by various factors that made the L* value calculated for the various scaled spectra change through a range of L* values similar to the experimental devices of Curves A through D. At the highest absorbance, the color coordinates L*, a*, b* were equal to 26.91, −3.62, −16.2. This medium has relatively small absolute values of a* and b* even though the value of L* is quite low. This small excursion in a*, b* for a large change in L* is indicative of a relatively gray medium. An experimental window with an electrochromic medium containing the electrochromic materials in the same relative concentrations shows a color coordinate excursion that is in excellent agreement with the excursion of the theoretical or calculated medium of FIG. 2 and the experimental device, as expected from the teachings of this invention, had a gray with slight blue-gray appearance.

For color coordinate curves like those in FIG. 5, it is interesting to note that a window containing the same electrochromic medium as a mirror will typically have a larger color coordinate excursion since the residual reflections that come into play in mirrors are not a significant factor in the apparent color of transmitted light for windows in their activated states. However, the color coordinate excursion for windows are certainly valuable in designing electrochromic media for mirrors and vice versa. A general observation is that the grayer a window appears when colored the smaller its color coordinate excursion from a*, b* equal 0,0 for coloration to a given L* value. The curves in FIG. 5 are nearly straight lines but do show some curvature. This is not unexpected as the Munsell loci of constant hue as a function of increasing chroma do show some curvature, see for example the figure of Page 63 and the associated discussion in Billmeyer and Saltzman ibid.

Figure 6:
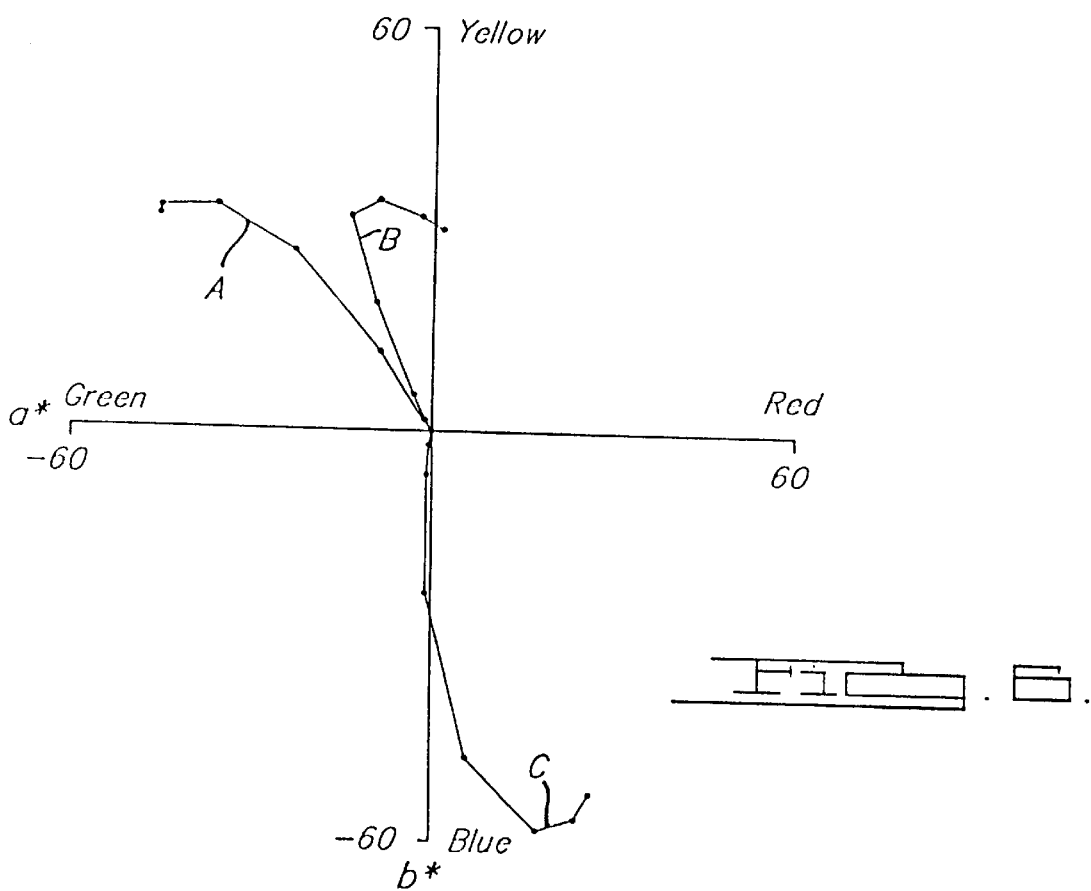
FIG. 6 shows several color coordinate curves indicating the staging phenomenon in electrochromic windows incorporating various electrochromic media as the windows are transitioned from their clear or high transmission states to their dark or low transmission states.

While some combinations of electrochromic materials maintain fairly consistent perceived color or hue even when the redox potentials are not similar, many do not. FIG. 6 shows the color coordinate curves ($D_{65}$/2-degree) for three windows that show various amounts of staging. Curve A of FIG. 6 is for an electrochromic medium in an electrochromic window filled with a propylene carbonate solution of 30 mM 5,10-dimethyl-5,10-dihydrophenazine, 15 mM 1,1'-bis(3-phenyl(n-propyl))-dipyridinium bis(tetrafluoroborate) and 15 mM 1,1'-ethylene-2,2'-dipyridinium bis (hexafluorophosphate). This later compound has a redox potential of −0.252 on the redox potential scale of the compounds of Table 1 through 9. Curve A starts at a*, b* equal 0, 0 at 0.0 volts and at higher voltages shows more curvature as compared to the curves in FIG. 5. For the window of Curve A, there is very little perceived change in hue or color appearance as a function of voltage. This is because the difference in redox potential between the two cathodic materials is 44 millivolts so they are still similar within the definition of this invention.

The electrochromic medium for which the data of Curve B was measured was contained in an electrochromic window filled with a propylene carbonate solution of 8 mM 5-ethyl-10-methyl-5,10-dihydrophenazine, 20 mM 5,10-dimethyl-5,10-dihydrodibenzo (A,C)phenazine and 34 mM 1,1'-ethylene-4,4'-dimethyl-2,2'-dipyridinium bis (hexafluorophosphate). This color coordinate curve shows significant curvature and the device shows readily distinguishable perceived colors, going from greenish/yellow at low voltage to reddish/brown at high voltages. The difference in redox potential between the two anodic materials is 80 millivolts and staging is readily apparent.

Curve C shows data for an electrochromic medium in an electrochromic window filled with 8 mM N,N,N',N'-tetramethyl-p-phenylenediamine, 20 mM 5,10-diisopropyl-5,10-dihydrophenazine and 34 mM 1,1'-bis(3-phenyl(n-propyl))-dipyridinium bis(tetrafluoroborate). The redox potentials of the anodic materials differ by 88 millivolts and the color coordinate curve shows significant curvature. The perceived color of the device changes only slightly from blue to blue-purple through the applied voltage range. The slight variation in perceived color or hue variation may be due to the fact that, at the voltages where the absorption spectra changes shape, the magnitude of the chroma is already quite high and L* is quite small, thus obscuring the change in hue.

The electrochromic medium comprises the electrochromic materials, and other materials like solvents, light absorbers, light stabilizers, thermal stabilizers, antioxidants, and a free standing gel (which includes a polymer matrix). The polymer matrix that may optionally be used in the present invention is a part of a free-standing gel that is disclosed in commonly assigned co-pending U.S. patent application Ser. No. 08/616,967, entitled "IMPROVED ELECTROCHROMIC LAYER AND DEVICES COMPRISING SAME" to W. L. Tonar et al. For electrochromic mirrors, the free-standing gel cooperatively interacts with glass elements 112 and 114 to produce a mirror that acts as one thick unitary member rather than two glass elements held together only by a seal member. This allows one to construct a rearview mirror with thinner glass in order to decrease the overall weight of the mirror while maintaining sufficient structural integrity so that the mirror will survive the extreme environments common to the automobile environment. For electrochromic windows (especially larger windows), the polymer matrix cooperatively interacts with glass elements 112 and 114 such that the hydrostatic pressure that typically occurs from gravity acting on the electrochromic medium (when the electrochromic medium includes a solution) is reduced or eliminated.

During operation of an electrochromic mirror in the clear state and having a third surface reflector, light rays enter through the front glass 112 and pass through the transparent conductive layer 116, the electrochromic medium in chamber 122, before being reflected by the reflector/electrode disposed on the third surface 114a (unless the mirror has a fourth surface reflector) of the mirror 110. Light in the reflected rays exit by the same general path traversed in the reverse direction. When a sufficiently high voltage (in come cases of the proper polarity) is applied to an electrochromic device, electrochemical reduction takes place by electron transfer to the electrochromic medium from one of the electrodes (designated as the cathode) and electrochemical oxidation takes place by electron transfer from the electrochromic medium to the other electrode (designated as the anode). The electrochemical reduction and/or the electrochemical oxidation give rise to a change in the light absorption properties of the material or materials reduced and/or oxidized. Operation, or activation, of the device generally results in an increase in light absorption at the wavelengths of interest (although it is possible for operation of an already colored device to result in a decrease in light absorption at the wavelengths of interest). When the device is in its dark state or some state between its dark and clear state, both the entering rays and the reflected rays are attenuated in proportion to the degree to which the electrochromic medium 124 is light absorbing.

Those skilled in the art will understand that the main difference between an electrochromic motor vehicle mirror and an electrochromic window or some other electrochromic device is the inclusion of a reflector for mirrors. By following the teachings outlined within the specification an electrochromic device may be produced having various preselected perceived colors, including gray, whether that device is a mirror, window, display, etc.

With respect to motor vehicle mirrors, FIG. 7 shows a front elevational view schematically illustrating an inside mirror assembly 110 and two outside rearview mirror assemblies 111a and 111b for the driver-side and passenger-side, respectively, all of which are adapted to be installed on a motor vehicle in a conventional manner and where the mirrors face the rear of the vehicle and can be viewed by the driver of the vehicle to provide a rearward view. Inside mirror assembly 110, and outside rearview mirror assemblies 111a and 111b may incorporate light-sensing electronic circuitry of the type illustrated and described in the above-referenced Canadian Patent No. 1,300,945; U.S. Pat. No. 5,204,778; or U.S. Pat. No. 5,451,822, and other circuits capable of sensing glare and ambient light and supplying a drive voltage to the electrochromic element. Mirror assemblies 110, 111a and 111b are essentially identical in that like numbers identify components of the inside and outside mirrors. These components may be slightly different in configuration but function in substantially the same manner and obtain substantially the same results as similarly numbered components. For example, the shape of the front glass element of inside mirror 110 is generally longer and narrower than outside mirrors 111a and 111b. There are also some different performance standards placed on inside mirror 110 compared with outside mirrors 111a and 111b. For example, inside mirror 110 generally, when fully cleared, should have a reflectance value of about 70 percent to about 80 percent or higher whereas the outside mirrors often have a reflectance of about 50 percent to about 65 percent. Also, in the United States (as supplied by the automobile manufacturers), the passenger-side mirror 111b typically has a spherically bent, or convex shape, whereas the driver-side mirror 111a, and inside mirror 110 presently must be flat. In Europe the driver-side mirror 111a is commonly flat or aspheric, whereas the passenger-side mirror 111b has a convex shape. In Japan both mirrors have a convex shape. The following description is generally applicable to all mirror assemblies of the present invention.

The electrical circuit preferably incorporates an ambient light sensor (not shown) and a glare light sensor 160, the glare light sensor being positioned either behind the mirror glass and looking through a section of the mirror with the reflective material completely or partially removed, or the glare light sensor can be positioned outside the reflective surfaces, e.g., in the bezel 144. Additionally, an area or areas of the electrode and reflector, such as 146 or the area aligned with sensor 160, may be completely removed, or partially removed in, for example, a dot or line pattern, to permit a vacuum fluorescent display, such as a compass, clock, or other indicia, to show through to the driver of the vehicle. Above-referenced co-pending U.S. Patent Application entitled "AN INFORMATION DISPLAY AREA ON ELECTROCHROMIC MIRRORS HAVING A THIRD SURFACE REFLECTOR" shows a presently preferred line pattern. The present invention is also applicable to a mirror which uses only one video chip light sensor to measure both glare and ambient light and which is further capable of determining the direction of glare. An automatic mirror on the inside of a vehicle, constructed according to this invention, can also control one or both outside mirrors as slaves in an automatic mirror system Rearview mirrors embodying the present invention preferably include a bezel 144, which extends around the entire periphery of each individual assembly 110, 111a and/or 111b. The bezel 144 conceals and protects the spring clips (not shown) and the peripheral edge portions of sealing member and both the front and rear glass elements (described below). A wide variety of bezel designs are well known in the art, such as, for example the bezel taught and claimed in above-referenced U.S. Pat. No. 5,448,397. There are also a wide variety of housings well known in the art for attaching the mirror assembly 110 to the inside front windshield of an automobile, or for attaching the mirror assemblies 111a and 111b to the outside of an automobile. A preferred housing for attaching an inside assembly is disclosed in above-referenced U.S. Pat. No. 5,337,948.

The materials that are described in Examples 1–29 are believed to be novel chemical substances except for the chemical substance of Examples 10 and 25. Certain properties of some of these materials are shown in Tables 1–9. These materials can be used as redox materials in such applications as redox batteries, redox indicators and mediated electron transfer in electro-organic synthesis. Because they significantly change their absorption spectra for visible light upon electrochemical reduction or electrochemical oxidation, they are also useful in electrochromic media for use in electrochromic windows, displays, mirrors, etc. In particular, these materials have colored state absorption spectra and redox potentials such that they can be placed in groups of materials with similar redox potentials. By selecting two or more materials with different colored state absorption spectra from a group with similar redox potentials, and by choosing relative concentrations of the two or more materials, one can design an electrochromic medium that has a pre-selected perceived color when incorporated in an electrochromic device and operated throughout the normal voltage range or transmission range of the device. These materials are also particularly useful in designing electrochromic media that result in electrochromic devices that have a perceived color of gray throughout their normal ranges of operation.

A number of the phenazine compounds listed in Tables 7 through 9 with the following general structure:

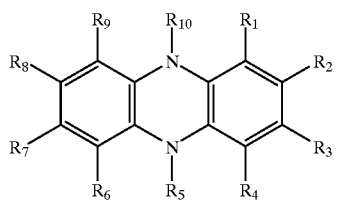

[XX]

have advantageous characteristics as compared to phenazines previously studied for inclusion in electrochromic media. Most phenazines previously studied have their main visible light absorption peak with its wavelength for maximum absorbance around 460 nanometers for the electrochemically activated state. Combination of a phenazine compound as the anodic material with a typical 1,1'-substituted-4,4'-dipyridinium salt as the cathodic material (with a wavelength for maximum absorbance of visible light around 600 nanometers for the electrochemically activated state), gives rise to electrochromic media which are poorly absorbing in the wavelength range from about 470 and to about 540 nanometers. These media and devices containing them typically have green-blue-green appearance in daylight and somewhat greenish-blue appearance when used in a rearview mirror to relieve glare during night driving.

Phenazine compounds have been discovered that have substantial visible light absorbance in the 470 to 540 nanometer range and, in fact, have their maximum visible absorbance peak in this range. Of particular note are the phenazine compounds with phenyl, phenoxy, vinyl, or substituted phenyl, e.g., tolyl, in one or more of the 2, 3, 7 and 8 positions. Remarkably, the normally electron withdrawing aryl groups listed above, have little if any effect on the redox potential for the first one electron oxidation of these compounds when substituted in these positions, and yet these groups red shift the absorption spectra of the oxidized or electrochemically activated state. Combining these novel phenazines in various relative concentrations with phenazines that absorb around 470 nanometers or less results in electrochromic media that have a desirable color appearance, including gray, when activated. In addition, phenazine compounds with aryl group substitution, e.g., phenyl, vinyl, tolyl, etc., in one or more of the 2, 3, 7 and 8 positions can be combined in electrochromic media without impacting the photochemical or thermal stability of the media. The only potential drawback is that the non-activated, neutral state of these compounds can be slightly yellow due to tailing of the UV absorbance of the non-activated state.

This concern is largely overcome by placing methyl or alkyl group(s) adjacent to or on the aryl substituent or on the aryl group in a position adjacent to the attachment between the phenazine and the aryl group. For example, 2,5,10-trimethyl-3-phenyl-5,10-dihydrophena, zine; 1,5,10-trimethyl-2-phenyl-5,10-dihydrophenazine; 2,7-di(o-tolyl)-5,10-dimethyl-5,10-dihydrophenazine and even 2,3-diphenyl-5,10-dimethyl-5,10-dihydrophenazine, (two adjacent aryl groups), are either colorless or less yellow than 2-phenyl-5,10-dimethyl-5,10-dihydrophenazine, 2,7-diphenyl-5,10-dimethyl-5,10-dihydrophenazine and 2-vinyl-5,10-dimethyl-5,10-dihydrophenazine. Other phenazines with wavelengths of maximum absorption in the range of 470 to 540 nanometers for their electrochemically activated state, without being substantially yellow in their non-activated state are very useful as well for combinations that achieve a pre-selected color, especially gray, (e.g. 2,7-diphenoxy-5,10-dimethyl-5,10-dihydrophenazine; 2-phenoxy-5,10-dimethyl-5,10-dihydrophenazine; and 5,10-diisopropyl-5,10-dihydrophenazine).

In example 17, 5,10-dimethyl-5,10-dihydrophenazine was made from phenazine in a novel one-pot synthesis. This same strategy can be applied to alkylation of phenazines, triphenodithiazines, triphenodioxazines, quinoxalinophenazines, phenazine-based dyes, phenoxazine-based dyes, phenothiazine-based dyes and similar phenazine compounds. In the general procedure, the azine starting material is both reduced and alkylated in the same reaction mixture. This procedure is novel because it teaches how to do both reduction and alkylation of the azine compound in a safe, rapid, cost-effective one-pot reaction.

In prior literature there are references to reducing and alkylating phenazines in separate steps and usually one of the steps is hazardous and expensive. In the reference, "The Direct Preparation of Some Dihydro and Other Phenazine Derivatives," *JACS* (1957) pp. 6178–6179, phenazine was reduced with sodium or potassium metal and was then alkylated with methyliodide. This method is hazardous, tedious and expensive. In another reference, "Preparation and Properties of Electron Donor Acceptor Complexes of the Compounds Having Capto-dative Substituents," *J. Heterocyclic Chemistry* (1989), Vol. 26, pp. 435–438, phenazine was reduced with sodium dithionite. The resulting dihydrophenazine was then alkylated by using butyl lithium for a lithium-proton exchange, and the dilithio adduct was alkylated with addition of methyl iodide. This process is a two-pot synthesis that involves a hazardous alkylation step.

In accordance with an embodiment of the present invention, the azine compound, reducing reagent, base, alkylating reagent and phase transfer catalyst are added together in a polar aprotic solvent with a small amount of water present. Upon heating the azine is both reduced and alkylated. We have applied our process to make many alkylated: phenazines, e.g. 2,7-diphenyl-5,10-dimethyl-5,10-dihydrophenazine; nitrogen heterocycles, e.g. N,N',N'',N'''-tetrabutylquinoxalinophenazine; azine-based dyes, e.g. 3,7-dibutoxy-10-butylphenoxazine from 7-hydroxy-3H-phenoxazin-3-one.

We have typically used sodium dithionite as the reducing reagent, however other reducing reagents may work as well e.g. hypophosphorous acid. Our base is usually potassium carbonate or sodium carbonate powder. Alkylating reagents can be alkyl iodides, bromides, chlorides, triflates, mesylates, or tosylates. The phase transfer catalyst is essential and we have had good success with quaternary ammonium halides or hydrogen sulfates. Crown ethers and quaternary phosphonium catalysts may work as well. The best catalysts have proven to be "accessible" quaternary ammonium salts, which is a term familiar to those skilled in the art of phase-transfer reactions. The best solvent is acetonitrile but other polar aprotic solvents may work. Also helpful to decrease reactions time is the addition of a small amount of water.

The procedure is as follows: For one mole of azine compound having two azine nitrogens, the amounts of other reagents used are: 1.15 moles of sodium dithionite (85%), 2.0 moles of sodium carbonate, 4.0 moles of alkyl halide, 0.115 moles of phase-transfer catalyst, 10 liters of acetonitrile, and 200 milliliters of water. Combine all reagents in one pot and heat to reflux under an inert atmosphere for a minimum of 5 hours. Add 10 liters of water and filter off alkylated product. These are the presently preferred amounts of these reagents, however, it is our intention to teach that because the reaction is robust, these reagents will work to produce alkylated product, even when the amounts of reagents are not present in the preferred amounts.

An alteration to these conditions is necessary when dialkylamino substituents are present. In this case a 2-phase reaction consisting of a non-polar organic solvent and an aqueous hydroxide layer are substituted for the acetonitrile/ water/carbonate combination in the above-mentioned process. This avoids quaternization of the dialkylamino groups.

Also it is important to note that alkyl iodides are more reactive than alkyl bromides and alkyl bromides are more reactive than alkyl chlorides. Sodium iodide can be added as a co-catalyst when using alkyl bromides or alkyl chlorides.

In conclusion, this one-pot reduction/alkylation process is widely applicable in alkylating phenazines and related azine compounds, as is shown in Examples 1, 3, 4, 12, 13, 14 and 16.

The dipyridinium compounds listed in Tables 1 through 6 are commonly referred to as viologens. In order to make viologens that are more difficult to electrochemically reduce, it is known to substitute the dipyridinium salts with alkyl groups at one or more of the 2, 2', 6 and 6' positions shown in the following general structure.

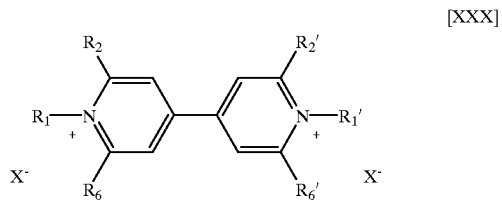

[XXX]

However, substitution with methyl groups in one or more of the 2, 2', 6 and 6' position leads to compounds with relatively acidic protons due to the strong electron withdrawing power of the quaternarized nitrogen near the methyl group. In addition, 1,1',2,2',6,6'-hexamethyl-4,4'-dipyridinium salts are only slightly soluble in polar organic solvents like cyclic esters and nitrites when the salt contains anions like tetrafluoroborate, hexafluorophosphate, perchlorate or halides. Example 29 describes the synthesis of viologens that overcome these difficulties and provide compounds that have diffusion characteristics that are desirable. Compounds of structure XXX with one or more of the 2,2',6 and 6' positions substituted with aralkyl group(s), e.g., 2-phenylethyl and 3-phenyl(n-propyl), or long chain alkyl group(s), e.g., hexyl, which have the other 2,2',6 and 6' positions substituted with methyl group(s) have increased solubility in polar organic solvents as compared to compounds of structure XXX which have methyl groups in each of the 2,2',6 and 6' positions.

In general, substitution of one or more of the 2, 2', 6 and 6' positions with 2-phenylethyl or 3-phenylpropyl results in a viologen which is more difficult to electrochemically reduce, does not have proton(s) as acidic as if the substitution were a methyl group and because it is believed that the phenyl groups are well solvated by solvents like propylene carbonate these compounds are believed to have smaller diffusion coefficients than similar viologens without these substitutions.

Certain aspects of the present invention are illustrated in more detail in the following examples. Unless specified otherwise, all concentrations cited in the examples are at room temperature (20–27 degrees Celsius) and all temperatures are in degrees Celsius.

EXAMPLE 1

Synthesis of 5-ethyl-10-methyl-5,10-dihydrophenazine 5-ethyl-10-methyl-5,10-dihydrophenazine was made as follows: 5-methylphenazinium methosulfate salt was reduced and alkylated to 5-ethyl-10-methyl-5,10-dihydrophenazine in a one-pot phase transfer reaction.

1.0 grams of the 5-methylphenazinium methosulfate salt was refluxed in a 2-phase slurry containing 50 milliliters of toluene, 10 milliliters of 4M aqueous NaOH, 10 grams of sodium dithionite, 10 milliliters of iodethane, 0.1 grams of tetrabutylammonium hydrogen sulfate and 50 milliliters of water.

This mixture was refluxed for 4 days after which the reaction was cooled and the lower aqueous layer separated and discarded. After two more water washes, the toluene was removed and the crude product redissolved in 50 milliliters of hot ethanol. The cooled solution produced 0.35 grams of 5-methyl-10-ethyl-5,10-dihydrophenazine for a 48% yield.

EXAMPLE 2

Synthesis of 2-vinyl-5,10-dimethyl-5,10-dihydrophenazine

A sample of 2-formyl-5,10-dimethyl-5,10-dihydrophenazine was prepared according to the procedure of Pokhodenko et.al., *J. Chem. Soc., Chem. Commun*, 1985, 72. The formyl group was converted to the vinyl group by the procedure of Ghosh and Spiro, *J. Electrochem. Soc.*, 128, 1281 (1981) for making 4-vinyl-1,10-phenanthroline. Recrystallization from acetone/water gave a yellow solid with mass 236 and electrochemistry consistent with an N,N'-dialkylated phenazine.

EXAMPLE 3

Synthesis of 2,7-bis(o-tolyl)-5,10-dimethyl-5,10-dihydrophenazine 2,7-bis(o-tolyl)-5,10-dimethyl-5,10-dihydrophenazine was prepared from 2,7-dichlorophenazine. The 2,7-dichlorophenazine was prepared from 2-iodo-5-chloronitrobenzene and 2-nitro-5-chloroaniline using an Ullmann type aryl amination, followed by reduction of the nitro groups and ferric chloride oxidation.

The o-tolyl groups were substituted for the chloro group at the 2,7-dichlorophenazine with a "Suzuki coupling" using o-tolyboronic acid. "Palladium Catalyzed Cross-Coupling Reactions of Organoboron Compounds", N. Miyawra and A. Suzuki, *Chem Rev*. 95, pp. 2457–2483 (1995). This cross-coupling reaction took about 3 weeks to go to completion.

The 2,7-bis(o-tolyl)phenazine (2.2 grams) was refluxed in acetonitrile containing 2% by volume water, 0.6 grams of methyltributyl ammonium chloride, 8.7 grams of sodium dithionite, 1.6 grams of sodium carbonate, and 3.1 milliliters of iodomethane. After 40 hours, water was dripped into the refluxing reaction solution and product precipitated out. After cooling, the product was filtered off and recrystallized from acetonitrile. 2.07 grams of product was isolated for an 87% yield for the alkylation.

EXAMPLE 4

Synthesis of 2,3-dimethyl-7-trifluoromethyl-5,10-diethyl-5,10-dihydrophenazine 2,3 dimethyl-7-trifluoromethyl-5,10-diethylphenazine was prepared from the 2,3-dimethyl-7-trifluoromethylphenazine.

The 2,3-dimethyl-7-trifluoromethylphenazine was prepared in a 3-step process, starting with 4,5-dimethyl-1,2-phenylenediamine and 3-nitro-4-bromobenzotrifluoride. The nucleophilic substitution product being the biarylamine was then reduced with stannous chloride in conc. HCl to the diamino diphenylamine.

This compound was oxidized to the phenazine with ferric chloride, in a dilute HCl aqueous solution. Tomlinson: "The Preparation of 2:2'-diaminodiphenyl Amines", *J. Chem. Soc.*, pp. 158–163 (1939).

24.0 grams of this phenazine was added to 500 milliliters of acetonitrile, 21.2 grams of sodium carbonate, 69.6 grams of sodium dithionite, 3.4 grams of tetrabutyl ammonium hydrogen sulfate and 78.0 grams of iodoethane. This mixture was refluxed for 4 days before it went to completion. 400 milliliters of water was slowly added to the refluxing reaction slurry. The desired product precipitated out and after cooling was filtered off. Product was recrystallized from hot ethanol yielding 17.7 grams of 2,3-dimethyl-7-trifluoromethyl-5,10-diethyl-5,10-dihydrophenazine. This is an overall yield of 30.1% starting from the 4,5-dimethyl-1,2-phenylenediamine.

EXAMPLE 5

Synthesis of 2,3,5,10-tetramethyl-7-trifluoromethyl-5,10-dihydrophenazine

This material was prepared by the procedure of Synthesis Example 4 with the exception that iodomethane was substituted for iodoethane in the alkylation step.

EXAMPLE 6

Synthesis of 2,3-diphenyl-5,10-dimethyl-5,10-dihydrophenazine 2,3-diphenylphenazine was prepared according to the method of C. H. Issidorides, et.al., *Tetrahedron* 34, 217 (1978). The phenazine nitrogens were then methylated by the procedure of Synthesis Example 3.

EXAMPLE 7

Synthesis of 2,5,10-trimethyl-3-phenyl-5,10-dihydrophenazine 2-methyl-3-phenylphenazine was prepared by the method of C. H. Issidorides, et.al., *Tetrahedron* 34, 217 (1978), except for that 1-phenyl-1,2-propanedione was substituted for benzil. The phenazine nitrogens were then methylated by the procedure of Synthesis Example 3.

EXAMPLE 8

Synthesis of 5,10-diisopropyl-5,10-dihydrophenazine

Phenazine, 9.0 grams, was stirred with 6.5 grams a finely divided metal alloy of 10:1 potassium to sodium, in 150 milliliters of 1,2-dimethoxyethane, at 40° C., until a brick red slurry was formed: approximately 24 hours. 2-bromopropane, 14.1 milliliters, was added and the reaction was allowed to stir for 2 hours at which time the reaction mixture was filtered, the filtrate was rotovaped to dryness and the product loaded as a solid onto a silica gel column. The column was prepared with and eluted with 8:2 hexane/ethylacetate. Removal of solvent from the target compound fractions gave a white solid which was recrystallized from methanol to give 2.1 grams of white needles, m.p. 80–81° C. A mass of 306 was confirmed by mass spectrometry.

EXAMPLE 9

Synthesis of 2,3,5,10-tetramethyl-5,10-dihydrobenzo(B)phenazine

The 2,3-dimethylbenzo(B)phenazine was prepared by the condensation of 2,3-diaminonapthalene with 4,5-dimethyl-1,2-benzoquinone in 4:1 ethanol to acetic acid at reflux for 2 hours. The phenazine was alkylated by the procedure of Synthesis Example 8, using iodomethane. Electrochemical analysis was consistent with an N,N'-dialkylated phenazine.

EXAMPLE 10

Synthesis of 5,10-dimethyl-5,10-dihydrodibenzo(A, C)phenazine

Dibenzo (A,C) phenazine was prepared with 1,2-phenylenediamine and phenanthrenequinone, using standard condensation conditions. Dibenzo(A,C)phenazine, 4.2 grams, was alkylated by the procedure of Synthesis Example 8, using methyl iodide to give 2.1 grams of yellow crystals. Electrochemical analysis was consistent with an N,N'-dialkylated phenazine.

EXAMPLE 11

Synthesis of 5,10-dimethyl-5,10-dihydrobenzo(A)phenazine

Benzo(A)phenazine was prepared with 1,2-phenylenediamine and 1,2-naphthoquinone, using standard condensation conditions.

This phenazine was reduced with a 3:1 potassium/sodium metal alloy in dimethoxyethane, to the brick red alkali metal adduct. Alkylation occurred over 1 hour with addition of iodomethane. Residual K/Na alloy was quenched with addition of ethanol. The product was isolated with column chromatography and was recrystallized from ethylacetate/hexane. 2.0 grams of product was isolated for a 38% overall yield.

EXAMPLE 12

Synthesis of 2-phenoxy-5,10-dimethyl-5,10-dihydrophenazine 2-phenoxy-5,10-dimethyl-5,10-dihydrophenazine was prepared from the 2-chlorophenazine. 2-chlorophenazine was prepared using 4-chloro-1,2-phenylenediamine and 1-iodo-2-nitrobenzene. This diphenylamine was reduced with stannous chloride to chloro-2,2'-diaminodiphenylamine and oxidized to the 2-chlorophenazine with ferric chloride in dilute aqueous HCl. "Tomlinson: The Preparation of 2:2'-Diaminodiphenylamines," *J. Chem. Soc.*, pp. 158–163 (1939).

2-chlorophenazine was reacted with potassium phenolate in tetraglyme to arrive at the 2-phenoxyphenazine. 150 milligrams of 2-phenoxyphenazine was refluxed in 50 milliliters of acetonitrile, 3 milliliters of iodomethane, 1.7 grams of sodium dithionite, 0.21 grams of sodium carbonate and 0.1 gram of tetrabutyl ammonium hydrogen sulfate. After 24 hours, reaction was complete. 50 milliliters of water was added to the refluxing reaction mixture. An oil separated out which was isolated and dissolved in 20 milliliters of hot ethanol. Upon cooling, 47 milligrams of crystalline 2-phenoxy-5,10-dimethyl-5,10-dihydrophenazine was isolated for a 31% yield.

EXAMPLE 13

Synthesis of 2,7-diphenoxy-5,10-dimethyl-5,10-dihydrophenazine 2,7-diphenoxy-5,10-dimethyl-5,10-dihydrophenazine was prepared from 2,7-dichlorophenazine. 2,7-dichlorophenazine was made from the procedure described in Synthesis Example 3 for 2,7-bis(o-tolyl)phenazine.

The diphenoxyphenazine was produced by reaction of the dichlorophenazine with potassium phenolate in tetraglyme. The resulting 2,7-diphenoxyphenazine 0.35 grams was refluxed in 100 milliliters of acetonitrile, 1.7 grams of sodium dithionite, 0.53 grams of sodium carbonate, 3 milliliters of iodomethane and 0.1 grams of tetrabutyl ammonium hydrogen sulfate. After refluxing for 3 days, 100 milliliters of water was added to the refluxing reaction slurry. The precipitated product was filtered off and recrystallized from ethanol. 210 milligrams of 2,7-diphenoxy-5,10-dimethyl-5,10-dihydrophenazine was isolated for a 55% yield.

EXAMPLE 14

Synthesis of 1,5,10-trimethyl-2-phenyl-5,10-dihydrophenazine 1,5,10-trimethyl-2-phenyl-5,10-dihydrophenazine was made with a 5-step process.

The first step involved a "Suzuki coupling" reaction with 2-nitro-6-bromo toluene and phenylboronic acid. The procedure used was from "Palladium Catalyzed Cross-Coupling Reactions of Arylboronic Acids with H-Deficient Heteroaryl Chlorides," *Tetrahedron*, 48, pp. 8117–8126 (1992). This reaction was quantitative after 40 hours.

The 2-nitro-6-phenyltoluene was isolated as an oil from the "Suzuki coupling." It was then reduced to the 2-amino-6-phenyltoluene with stannous chloride in concentrated HCl and methanol.

The next step is an Ullmann type aryl amination of the amine with 2-iodonitrobenzene. This reaction was carried out in nitrobenzene with copper as a catalyst. Product was isolated by distillation of the solvent followed by column chromatography.

The resulting 2-nitrodiphenylamine was isolated as an impure oil and was cyclized to the 1-methyl-2-phenylphenazine with iron powder. "Direct Ring Closure Through a Nitro Group I. Certain Aromatic Compounds with the Formation of Nitrogen Heterocycles: A New Reaction," by H. C. Waterman and D. L. Vivian, *J. Org. Chem.*, 14, 289–297 (1949).

The 1-methyl-2-phenylphenazine was carried on to the final reduction/alkylation step as an oil. The oil was refluxed in 50 milliliters of acetonitrile, 1 milliliter of water, 0.9 grams of methyltributyl ammonium chloride, 2.1 grams of sodium carbonate, 8.7 grams of sodium dithionite and 2 milliliters of iodomethane. After 16 hours, the reaction was quenched by adding 50 milliliters of water to the refluxing reaction mixture. An oil separated which was isolated, then dissolved in ethyl acetate and washed with water. The ethyl acetate was removed and the oil cleaned up with column chromatography. Recrystallization from ethanol yielded 88 milligrams of 1,5,10-trimethyl-2-phenyl-5,10-dihydrophenazine as a nearly white solid.

EXAMPLE 15

Synthesis of 2-phenyl-5,10-dimethyl-5,10-dihydrophenazine 2-phenyl-5,10-dimethyl-5,10-dihydrophenazine was prepared in a 4-step process.

The first step involves aryl amination of 4-bromo-3-nitrobiphenyl with aniline, in dimethylformamide. The resulting 2-nitro-4-phenyldiphenylamine was ring closed to the 2-phenylphenazine using sodium ethoxide and sodium borohydride by the procedure described in "A New Phenazine Synthesis, The Synthesis of Griseolutein Acid, Griseolutein A, and Methyl Diacetyl Griseolutein B", *J. Chem. Soc. Chem. Commun.*, 1423–1425 (1970).

The 2-phenylphenazine was reduced to the 2-phenyl-5,10-dihydrophenazine by adding aqueous dithionite solution to a refluxing ethanol solution of the phenazine. This dihydro product was isolated and then alkylated in a refluxing solution of acetonitrile containing iodomethane and sodium carbonate. Product was precipitated out by addition of water and was isolated. It was carbon treated and recrystallized from a mixture of acetone and ethanol to yield a bright yellow crystalline solid.

EXAMPLE 16

Synthesis of 2,7-diphenyl-5,10-dimethyl-5,10-dihydrophenazine 2,7-diphenyl-5,10-dimethyl-5,10-dihydrophenazine was prepared from 2,7-dichlorophenazine. 2,7-dichlorophenazine was made from the procedure described in Synthesis Example 3 for 2,7-bis(o-tolyl)phenazine.

The 2,7-diphenylphenazine was made from a "Suzuki" cross-coupling reaction with 2,7-dichlorophenazine and phenylboronic acid. Refer to the procedure described in "Palladium Catalyzed Cross-Coupling Reactions of Arylboronic Acids With Deficient Hetcroarylchlorides," *Tetrahedron*, 48, pp. 8117–8126.

660 milligrams of 2,7-diphenylphenazine was reduced and alkylated by refluxing in 10 milliliters of acetonitrile, 0.2 milliliters of water, 1 milliliter iodomethane, 3.5 grams of sodium dithionite, 0.21 grams of sodium carbonate and 60 milligrams of methyl-tributyl ammonium chloride. After 40 hours the reaction was quenched by dripping in 20 milliliters of water to the refluxing reaction slurry. 450 milligrams of 2,7-diphenyl-5,10-dimethyl-5,10-dihydrophenazine was isolated for a 62.0% yield.

EXAMPLE 17

Novel Method of Making 5,10-dimethyl-5,10-dihydrophenazine 5,10-dimethyl-5,10-dihydrophenazine can be easily made in a novel one-pot synthesis beginning with phenazine. In this synthesis, both reduction and alkylation proceed rapidly under mild reaction conditions.

Under a nitrogen atmosphere, 650 grams of phenazine was refluxed in 3.5 liters of acetonitrile with 100 milliliters of water, 899 milliliters of iodomethane (alkylating reagent), 765 grams of sodium carbonate powder (base), 723 grams of sodium dithionite (reducing reagent) and 130 grams of methyltributyl ammonium chloride (phase-transfer catalyst) present. Phenazine was completely reduced and methylated after 5 hours. At this time 4.5 liters of water was added to the refluxing reaction slurry over 25 minutes. Upon cooling to room temperature, nearly all of the 5,10-dimethyl-5,10-dihydrophenazine had precipitated. This was filtered off and redissolved in 1.95 liters of hot toluene. This toluene solution was filtered to remove inorganic salts. After filtration, 0.95 liters of toluene was removed via atmospheric distillation under nitrogen. The reaction was cooled to 85° C. and 1 liter of ethanol was added over 20 minutes.

The solution was cooled gradually to room temperature and kept at room temperature for 4 hours before filtering. The resulting 5,10-dimethyl-5,10-dihydrophenazine was washed with 1 liter of water followed by 1 liter of cold ethanol. This product was then dried to 650.2 grams of a white crystal for an 85.3% yield.

EXAMPLE 18

Synthesis of 1-methyl-1'-phenyl-4,4'-dipyridinium bis(hexafluorophosphate)

1-phenyl-1'-methyl-4,4'-dipyridinium bis (hexafluorophosphate) was made by first attaching the phenyl group and then the methyl group to 4,4'-dipyridyl. The phenyl group was attached using a procedure from the Canadian Patent #1031346 entitled, "Preparation of Bipyridinium Compounds" by John G. Allen. The 4,4'-dipyridyl is quaternized with 2,4-dinitrochlorobenzene at 35° C.; and using only 1 equivalent at this temperature limits the quaternization to just one side of the 4,4'-dipyridyl.

The monoquaternarized intermediate is refluxed with 10 equivalents of iodomethane, in acetonitrile, to quaternize the remaining nitrogen. This reaction is complete after 1 hour with a 97.6% yield. The mixed salt is dissolved in hot water, filtered and product precipated out with addition of a 1 molar ammonium hexafluorophosphate solution.

EXAMPLE 19

Synthesis of 1-(4-cyanophenyl)-1'-methyl-4,4'-bipyridinium bis(hexafluorophosphate)

1-(4-cyanophenyl)-1'-methyl-4,4'-bipyridinium-bis (hexafluorophosphate) was made similarly to 1-phenyl-1'-methyl-4,4'-dipyridinium-bis(hexafluorophosphate) in synthesis Example 18. The only difference is that 4-cyanoaniline was used to displace the 2,4-dinitrophenyl group instead of aniline. See Canadian Patent No. 1031346.

EXAMPLE 20

Synthesis of 1-(4-methoxyphenyl)-1'-methyl-4,4'-dipyridinium bis(hexafluorophosphate)

1-(4-methoxyphenyl)-1'-methyl-4,4'-dipyridinium bis (hexafluorophosphate) was made similarly to 1-methyl-1'-phenyl-4,4'-dipyridinium bis(hexafluorophosphate) in Synthesis Example 18. The only difference is that para-anisidine was used to displace the 2,4-dinitrophenyl group instead of aniline. See Canadian Patent #1031346.

EXAMPLE 21

Synthesis of 1-phenyl-1'-(4-dodecylphenyl)-4,4'-dipyridinium bis(hexafluorophosphate)

This viologen was made with reference to Canadian Patent #1031346. First the 4,4'-dipyridyl was quaternarized on one side at 35° C. with 1 equivalent of 2,4-dinitrochlorobenzene. After displacement with dodecylaniline, the second nitrogen was quaternized with dinitrochlorobenzene. This quatemization was done with an excess of dinitrochlorobenzene at reflux temperature. This dinitrophenyl group was then displaced with aniline to give the dichloride salt of the desired product. Metathesis to the hexafluorophosphate was done in hot MeOH with an acetonitrile solution of ammonium hexafluorophosphate.

EXAMPLE 22

Synthesis of 1,2,6-trimethyl-1'-phenyl-4,4'-dipyridinium bis(tetrafluoroborate)

2,6-dimethyl-4,4'-dipyridyl was quaternized with a 5-fold excess of dinitrochlorobenzene at 50° C. The quaternization takes place at the unhindered nitrogen to yield 2,6-dimethyl-1'-(2,4-dinitrophenyl)-4,4'-dipyridinium chloride. This is reacted with aniline (see Canadian Patent #1031346) to give 2,6-dimethyl-1'-phenyl-4,4'-dipyridinium chloride.

Finally the hindered nitrogen is quaternized with a 20-fold excess of iodomethane in refluxing acetonitrile. This quaternization is done after 1 hour and the resultant di-substituted dipyridinium salt is filtered off. This salt is dissolved in hot water and precipitated as the tetrafluoroborate salt with a 1 molar aqueous solution of sodium tetrafluoroborate.

EXAMPLE 23

Synthesis of 1,1'-bis(2,6-dimethylphenyl)-4,4'-dipyridinium bis(tetrafluoroborate)

7.0 ml of 2,6-dimethylaniline was added to 40 ml of a 3:2 dimethylformamide/$H_2O$ solution and the mixture was heated to reflux under a nitrogen atmosphere. 5.0 g of 1,1'-bis(2,4-dinitrophenyl)-4,4'-dipyridinium ($Cl^-$ salt) in 50 ml water was slowly added (over 20 min) via a pressure-equalizing addition funnel. The black solution was refluxed for an additional 2.5 h, then cooled to produce a yellow-brown oily precipitate. The solid material was removed by filtration and discarded. The volume of the filtrate reduced to ca. 10 ml by rotary evaporation. Addition of copious amounts of acetone produced a light brown solid which was redissolved in 10:1 methanol/water. This solution was treated with decolorizing charcoal and filtered. Aqueous sodium tetrafluoroborate was added and the solution was allowed to stand at room temperature overnight. The product was isolated as light brown needles by vacuum filtration.

EXAMPLE 24

Synthesis of 1,1'-bis(3,5-dimethylphenyl)-4,4'-dipyridinium bis(tetrafluoroborate)

6.7 ml of 3,5-dimethylaniline was added to 30 ml of a 3:2 dimethylformamide/$H_2O$ solution and the mixture was heated to reflux under a nitrogen atmosphere. 5.0 g of 1,1'-bis(2,4-dinitrophenyl)-4,4'-dipyridinium ($Cl^-$ salt) in 50 ml water was slowly added (over 20 min) via a pressure-equalizing addition funnel. The black solution was refluxed for an additional 5 h, then cooled to produce a yellow-brown precipitate. The solid material was removed by filtration and discarded. The volume of the filtrate reduced to ca. 10 ml by rotary evaporation. Addition of copious amounts of acetone produced an orange-brown solid which was redissolved in water. Aqueous sodium tetrafluoroborate was added, resulting in precipitation of the crude product as an orange solid. The product was purified first by digestion in ethanol, then by decolorizing charcoal treatment in methanol/acetonitrile. Following addition of water and removal of methanol and acetonitrile by rotary evaporation, the pure product was isolated as a chalky off-white solid by vacuum filtration.

EXAMPLE 25

Synthesis of 1,1'-bis(2,4,6-trimethylphenyl)-4,4'-dipyridinium bis(tetrafluoroborate)

7.5 ml of 2,4,6-trimethylaniline was added to 40 ml of a 3:2 dimethylformamide/$H_2O$ solution and the mixture was heated to reflux under a nitrogen atmosphere. 5.0 g of 1,1'-bis(2,4-dinitrophenyl)-4,4'-dipyridinium ($Cl^-$ salt) in 50 ml water was slowly added (over 20 min) via a pressure-equalizing addition funnel. The black solution was refluxed for an additional 6 hours, then cooled to produce a yellow-brown precipitate. The solid material was removed by filtration and discarded. The volume of the filtrate reduced to ca. 10 ml by rotary evaporation. Addition of copious amounts of acetone produced a yellow-brown solid which was redissolved in 10:1 methanol/water. Aqueous sodium tetrafluoroborate was added, causing formation of a bright yellow precipitate. The crude solid was isolated by vacuum filtration and washed with small portions of cold methanol and water. Purification was achieved by decolorizing charcoal treatment in methanol/acetonitrile.

Following addition of water and removal of methanol and acetonitrile by rotary evaporation, the pure product was isolated as a bright yellow solid by vacuum filtration.

EXAMPLE 26

Synthesis of 1-(3,5-dimethoxyphenyl)-1'-methyl-4,4'-dipyridinium bis(hexafluorophosphate)

3.0 ml of 3,5-dimethoxyaniline was added to 25 ml of a 3:2 dimethylformamide/$H_2O$ solution and the mixture was heated to reflux under a nitrogen atmosphere. 3.0 g of 1-(2,4-dinitrophenyl)-4,4'-dipyridinium ($Cl^-$ salt) in 50 ml water was slowly added (over 20 min) via a pressure-equalizing addition funnel. The orange-brown solution was refluxed for an additional 3 h, then cooled to produce a yellow precipitate. The solid material was removed by filtration and discarded. The volume of the filtrate reduced to ca. 10 ml by rotary evaporation. Addition of copious amounts of acetone produced a light yellow solid.

0.30 g of this solid was dissolved in 80 ml of acetonitrile, along with an excess of methyl iodide. The solution was refluxed under a nitrogen atmosphere for 4 h and then allowed to cool to room temperature. The resulting precipitate was isolated as a bright orange solid by vacuum filtration. This crude product (as a mixed $Cl^-$, $I^-$ salt) was redissolved in water. Aqueous sodium tetrafluoroborate was added and the solution was refrigerated overnight. The product was isolated as a yellow-orange solid by vacuum filtration. Purification was achieved by first redissolving in acetonitrile, then precipitating as the chloride salt by addition of a solution of tetraethylammonium chloride in acetone. The chloride salt was isolated by filtration and briefly air-dried. The product was then converted to the $PF_6^-$ salt by dissolving in water, filtering, and adding aqueous ammonium hexafluorophosphate to the filtrate. The resulting precipitate was isolated as a chalky, off-white solid by vacuum filtration. The color of this compound was less yellow than 1-(4-methoxyphenyl)-1'-methyl-4,4'-dipyridinium bis(hexafluorophosphate). This has advantages in electrochromic devices when residual yellow color is undesirable.

EXAMPLE 27

Synthesis of 1-methyl-1'-(2-methylphenyl)-4,4'-dipyridinium bis(hexafluorophosphate)

3.0 ml of o-toluidine was added to 25 ml of a 3:2 dimethylformamide/$H_2O$ solution and the mixture was heated to reflux under a nitrogen atmosphere. 3.0 g of 1-(2,4-dinitrophenyl)-4,4'-dipyridinium ($Cl^-$ salt) in 50 ml water was slowly added (over 20 min) via a pressure-equalizing addition funnel. The orange-brown solution was refluxed for an additional 3.5 h, then cooled to produce a yellow precipitate. The solid material was removed by filtration and discarded. The volume of the filtrate reduced to ca. 10 ml by rotary evaporation. Addition of copious amounts of acetone produced a light yellow solid which was redissolved in water. Aqueous ammonium hexafluorophosphate was added and the resulting white precipitate was isolated by vacuum filtration, washed with water, and dried in a vacuum oven.

0.70 g of this solid was dissolved in 50 ml of acetonitrile, along with ca. 1.0 g of methyl iodide. The solution was refluxed under a nitrogen atmosphere for 6 h. Addition of dilute aqueous ammonium hexafluorophosphate, followed by removal of acetonitrile by rotary evaporation, produced a light tan solid.

EXAMPLE 28

Synthesis of 1-methyl-1'-(2,4,6-trimethylphenyl)-4,4'-dipyridinium bis(hexafluorophosphate)

This compound was prepared from 1-(2,4-dinitrophenyl)-4,4'-dipyridinium chloride (see Synthesis Example 18) by reaction with excess methyl iodide in refluxing acetonitrile. The 2,4-dinitrophenyl group was then displaced by reaction with 2,4,6-trimethylaniline in 1:1 dimethylformamide/water (see Canadian Patent #1031346). The crude product was isolated as a mixed halide salt by reducing the volume of the reaction mixture to only a few ml, adding 200 ml of acetone, and refrigerating overnight. The resulting solid was isolated by filtration, redissolved in water, and precipitated as the hexafluorophosphate salt by addition of aqueous ammonium hexafluorophosphate.

EXAMPLE 29

Preparation of Novel 2,2',6,6'-substituted-4,4'-dipyridinium Salts

The procedure described here for preparing Compounds I–IV and VIII–XI are based on those outlined in:

1. (a) Minisci, *Top, Curr. Chem.*, Vol. 62, (1976), pp. 1–48
   (b) Synthesis, (1973) pp. 1–24
2. Minisci, Mondelli, Gardini and Porta, *Tetrahedron*, Vol. 28, (1972), 2403
3. Citterio, Minisci and Franchi, *J. Org. Chem.*, Vol. 45, (1980), 4752
4. Anderson and Kochi, *J. Am. Chem. Soc.*, Vol. 92, (1970), 1651
5. Baltrop and Jackson, *J. Chem. Soc., Perkin II*, (1984), pp 367–371

Preparation of 2-(2-phenylethyl)-4,4'-dipyridyl (I) and 2,2'-bis(2-phenylethyl)-4,4'-dipyridyl (II)

Procedure: To a stirring solution of 4,4'-dipyridyl (15.62 g; 0.1 mole) in a mixture of water (100 mL) and concentrated sulfuric acid (5.3 mL) were added hydrocinnamic acid (32.0 g; 0.213 mole) and silver nitrate (1.7 g; 0.01 mole) and the mixture was heated to about 80° C. and while maintaining this temperature for 30 minutes ammonium peroxy disulfate (22.82 g; 0.1 mole) was added in small portions. After the addition, the mixture was maintained at the same temperature for an additional 2 hours. Then the reaction mixture was cooled to the room temperature and was neutralized with aqueous sodium hydroxide (10%). The resulting dark brown-colored mixture was filtered and the filtrate was extracted several times with 25 mL portions of ethyl acetate. The organic layers were combined, dried over anhydrous magnesium sulfate, filtered and the filtrate was evaporated to remove the solvent completely so that a dark-colored viscous oil was left behind. From this oily mixture, the desired compounds I and II were isolated as solids by silica gel column chromatography. The respective amounts of I and II so obtained were 4.7g and 1.76g.

Preparation of 2-(3-phenyl(n-propyl))-4,4'-dipyridyl (III) and 2,2'-bis(3-phenyl(n-propyl)-4,4'-dipyridyl (IV)

Procedure: Compounds III and IV were prepared by the same procedure as described for the preparation of Compounds I and II except for using 4-phenyl butyric acid in place of hydrocinnamic acid. The respective amounts of III and IV so obtained were 3.3 g and 2.15 g.

Preparation of: 2,2',6-trimethyl-6'-(2-phenylethyl)-4,4'-dipyridyl (V); 2,2'-dimethyl-6,6'-bis(2-phenylethyl)-4,4'-dipyridyl (VI) and 2-methyl-2',6,6'-tris(2-phenylethyl)-4,4'-dipyridyl (VII)

Procedure: To a stirred suspension of sodium amide (29.2 g; 0.75 mole) in m-xylene (80 mL) was added 2,2',6,6'-tetramethyldipyridyl (5.3 g; 0.025 mole) under an argon atmosphere. After brief stirring, benzyl chloride (50 g; 0.39 mole) was added slowly over a period of 15–30 minutes and the mixture was refluxed for 15–20 hours. After this time the heating was stopped, the reaction mixture was cooled to room temperature and cold water (5–10 mL) was added cautiously to destroy the unreacted sodium amide. The mixture was acidified with concentrated hydrochloric acid and was extracted with methylene chloride a few times with 25 mL portions. This operation helped to remove the unreacted benzyl chloride and m-xylene solvent. The organic layer was separated and discarded. Now the aqueous solution was basified with sodium hydroxide (20% aqueous solution) and the mixture was extracted 2–3 times with 25 mL portions of methylene chloride. The organic layers were combined, dried over anhydrous magnesium sulfate and filtered. The filtrate on complete evaporation of the solvent gave rise to a brown viscous oil (9.2 g). The desired Compounds V, VI and VII were isolated from the mixture by silica gel column chromatography.

Preparation of 2,2',6-trimethyl-6'-n-hexyl-4,4'-dipyridyl (VIII) and 2,2'-dimethyl-6,6'-bis(n-hexyl)-4,4'-dipyridyl (IX)

Procedure: To a magnetically stirred solution of 2,2'6,6'-tetramethyl-4,4'-dipyridyl (5.3 g; 0.025 mole) in pure tetrahydrofuran (80 mL) cooled to –78° C. (dry ice and 2-propanol) was added under an argon atmosphere a cyclohexane solution (2.0 M) of n-butyl lithium (1.76 g; 0.0275 mole) from a dropping funnel over a period of 20 minutes. The solution turned deep blue immediately. The mixture was allowed to warm up to –30° C. for 5 minutes and was cooled back to –78° C. A solution of 1-chloropentane (2.93 g; 0.0275 mole) in pure tetrahydrofuran (15 mL) was now added from a dropping funnel over a period of 10 minutes. After the addition, the color of the mixture became dark purple. After stirring at –78° C. for a short period, the mixture was allowed to warm up to room temperature. Pure water (2–3 mL) was added cautiously to destroy any unreacted butyl lithium still present and the mixture was diluted with more pure water (100 mL) and was extracted 2–3 times with 25 mL portions of ethyl acetate. The organic layers were combined, dried over anhydrous magnesium sulfate, filtered, and the filtrate was evaporated to remove the solvent completely. This gave 7.2 g of a yellow-brown oil. Compounds VIII and IX were isolated from the oil by silica gel column chromatography as solid products.

Preparation of 2,2',6-trimethyl-6'-(3-phenyl(n-propyl))-4,4'-dipyridyl (IX) and 2,2'-dimethyl-6,6'-bis(3-phenyl(n-propyl))-4,4'-dipyridyl (X).

Procedure: The Compounds X and XI were prepared in the same way as described for the preparation of Compounds VIII and IX except for using 1-bromo-2-phenylethane in place of 1-chloropentane as the alkylating agent.

Conversion of Compounds I through XI to their Respective 1,1'-dimethyl-4,4'-dipyridinium diiodide Salts The diiodide salts of Compounds I through X were prepared by refluxing each of these with an excess mole equivalent of iodomethane in pure acetonitrile for 24 to 48 hours, and the resulting diquaternary salts were filtered, washed thoroughly with fresh acetonitrile, followed by rinsing with dry acetone.

Conversion of Compounds I–IV, VIII and IX to their Respective 1,1'-dimethyl-4,4'-dipyridinium bis (hexafluorophosphate) Salts Typical Procedure: The diiodide salt (5 mole) prepared as described above was dissolved in pure water (100–150 mL) and the solution was stirred with decolorizing carbon (1.0 g) for 2–3 hours at room temperature. The suspension was filtered and the colorless filtrate was treated with an aqueous solution of one molar ammonium hexafluorophosphate until the precipitation was complete. After standing for 1 hour, the precipitate was filtered with suction, washed with pure water (20 mL) 2–3 times and was recrystallized from water to obtain pure salt. The yields varied with the individual compounds anywhere from 20–80%.

Conversion of Compound VI to the 1,1'-dimethyl-4,4'-dipyridinium diperchlorate Salt The diiodide salt of Compound VI as prepared above was first dissolved in hot pure water (100 mL) and to the solution an aqueous solution (5%) of sodium perchlorate was added until the precipitation is complete. The precipitate was filtered, washed 4–5 times with pure water (25 mL) and the wet precipitate was recrystallized and purified by treatment with decolorizing carbon in a mixture (8:2 v/v) of acetonitrile and water. The yield of yellow-colored solid was 32%.

Conversion of Compound VII and VIII to the 1,1'-dimethyl-4,4'-dipyridinium bis(tetrafluoroborate) salt The diiodide salt (2.0 g; 3.5 m mole) was dissolved in pure water (25 mL) at room temperature. The solution was treated with decolorizing carbon, filtered and to the colorless filtrate was added an aqueous solution of sodium tetrafluoroborate (2 molar) until the precipitation was complete. The resulting light yellow-colored precipitate was filtered, washed 4–5 times with 25 mL portions of pure water. The solid precipitate was then recrystallized from hot water to obtain a colorless solid.

EXAMPLE 30

Green/Blue Electrochromic Device

Symmetrically substituted aryl viologens were prepared from reaction of the appropriate aniline derivative with 1,1'-bis(2,4-dinitrophenyl)-4,4'-dipyridinium as has been previously described in Examples 23 and 24. Ferrocene was obtained commercially (Aldrich) and purified by sublimation prior to use.

Two stock solutions, one containing 60 mM ferrocene in propylene carbonate and the second containing 30 mM each 1,1'-bis(2,4,6-trimethylphenyl)-4,4'-dipyridinium bis (tetrafluoroborate) and 1,1'-diphenyl-4,4'-dipyridinium bis (tetrafluoroborate) in propylene carbonate were prepared in separate small vials. Both stock solutions were deoxygenated with dry nitrogen. Equal volumes of each stock solution were introduced into a clean vial to produce a mixture which was approximately 30 mM in ferrocene and 15 mM in each of the two viologen derivatives. This multi-component mixture was then used to fill electrochromic devices.

Electrochromic window devices were fabricated as is known in the art with TEC-20 glass from Libbey-Owens-Ford with a 137 micrometer cell spacing. The devices were about 1'×2" in area and were filled by introducing the solution described above into the device through one of two holes drilled in the top plate. Both holes were then plugged using a hot glue gun.

Application of 1.2 V across this electrochromic device resulted in uniform coloration to a green/blue state; however some staging (through a green intermediate) was observed on both coloring and clearing.

EXAMPLE 31

Gray Electrochromic Device

Two stock solutions, one containing 60 mM ferrocene in propylene carbonate and the second containing 30 mM each 1,1'-bis(2,4,6-trimethylphenyl)-4,4'-dipyridinium bis(hexafluorophosphate) and 1-(4-cyanophenyl)-1'-methyl-4,4'-dipyridinium bis(tetrafluoroborate) in propylene carbonate were prepared in separate small vials. Both stock solutions were deoxygenated with dry nitrogen. Equal volumes of each stock solution were introduced into a clean vial to produce a mixture which was approximately 30 mM in ferrocene and 15 mM in each of the two viologen derivatives. This multi-component mixture was then used to fill electrochromic devices.

Electrochromic window devices were fabricated as is known in the art with TEC-20 glass from Libbey-Owens-Ford with a 137 micrometer cell spacing. The devices were about 1'×2" in area and were filled by introducing the solution described above into the device through one of two holes drilled in the top plate. Both holes were then plugged using a hot glue gun.

Application of 1.2 V across this electrochromic device resulted in uniform coloration to a dark blue/green (moderately gray) state. No staging was observed during either coloring or clearing.

EXAMPLE 32

Electrochromic Devices having Colors Ranging from Green/Gray and Blue-green Gray Three stock solutions, one containing 60 mM ferrocene in propylene carbonate, one containing 60 mM 1,1'-bis(2,4,6-trimethylphenyl)-4,4'-dipyridinium bis(tetrafluoroborate) (V1) in propylene carbonate and one containing 60 mM 1,1'-bis(3,5-dimethylphenyl)-4,4'-dipyridinium bis(tetrafluoroborate) (V2) in propylene carbonate were prepared in separate small vials. All three stock solutions were deoxygenated with dry nitrogen. Aliquots from each of the stock solutions were introduced into five clean vials in such a manner to produce the following solutions:
A) 30 mM ferrocene/15 mM V1 w/15 mM V2
B) 30 mM ferrocene/18 mM V1 w/12 mM V2
C) 30 mM ferrocene/20 mM V1 w/10 mM V2
D) 30 mM ferrocene/21 mM V1 w/9 mM V2
E) 30 mM ferrocene/24 mM V1 w/6 mM V2
These multi-component mixtures were then used to fill electrochromic devices.

Electrochromic window devices were fabricated as is known in the art with TEC-20 glass from Libbey-Owens-Ford with a 137 micrometer cell spacing. The devices were about 1'×2" in area and were filled by introducing the solutions described above into the device through one of two holes drilled in the top plate. Both holes were then plugged using a hot glue gun.

Application of 1.2 V across each of these electrochromic devices resulted in uniform coloration, with the exact color when full dark varying smoothly from greengray for device A to blue-green gray for device E. Slight staging was observed during coloring of A, B, and C, while D and E exhibited no appreciable staging during coloring or clearing.

EXAMPLE 33

Gray Electrochromic Devices

A solution consisting of 25 mM 1,1'-dimethylferrocene, 100 mM 2-hydroxy-4-methoxybenzophenone (as a UV stabilizer), 18 mM 1,1'-bis(2,6-dimethylphenyl)-4,4'-dipyridinium bis(tetrafluoroborate), 12 mM 1,1'-bis(3,5-dimethylphenyl)-4,4'-dipyridinium bis(tetrafluoroborate), and 3% (wt/wt) of polymethylmethacrylate in propylene carbonate was deoxygenated with dry nitrogen.

Electrochromic window devices were fabricated as is known in the art with TEC-20 glass from Libbey-Owens-Ford with a 137 micrometer cell spacing. Similarly, electrochromic mirrors were fabricated using a transparent TEC-20 front plate with either a TEC-20 back plate which had been previously silvered on the side opposite the conductive coating (fourth surface reflector) or coated with another reflective metal (third surface reflector). These devices measured about 2"×5" and were filled with the electrochromic solution described above via the vacuum backfilling technique. The vacuum fill ports of the devices were plugged with a UV cure material.

After four months, representative $L^*a^*b^*$ (A/2-degree) values were as follows:

|  | initial | | | darkened | | |
|---|---|---|---|---|---|---|
|  | $L^*$ | $a^*$ | $b^*$ | $L^*$ | $a^*$ | $b^*$ |
| fourth surface reflector | 87.51 | −1.42 | +12.60 | 32.96 | −0.37 | −6.27 |
| third surface reflector | 78.17 | +0.07 | +10.21 | 30.44 | −5.12 | −3.68 |

EXAMPLE 34

Gray Electrochromic Device

An electrochromic device was prepared from two pieces of TEC 15 glass spaced apart by 137 microns by a perimeter epoxy seal. The device was filled with a nitrogen purged propylene carbonate solution of 14 mM 5,10-diisopropyl-5,10-dihydrophenazine, 14 mM 5,10-dimethyl-5,10-dihydrobenzo(A,C)phenazine and 34 mM bis(3,5-dimethylphenyl)-4,4'-dipyridinium bis(tetrafluoroborate). In the clear state the device was slightly yellow and with 0.8 volts applied, the device was very dark gray. From the spectrum of the clear state, the color coordinates (A/2-degree) $L^*$, $a^*$, $b^*$ were found to be equal to 89.19, −0.27, 10.7 and at 0.8 volts $L^*$, $a^*$, $b^*$ were equal to 17.72, 9.03, 7.37.

The CIE curve white light transmittances were 75% clear and 2.5% darkened at 0.8 volts. Not only was the device gray when activated, it was remarkably low in transmission when fully darkened.

While the invention has been described in detail herein in accordance with certain preferred embodiments thereof,

What is claimed is:

1. A compound having the formula:

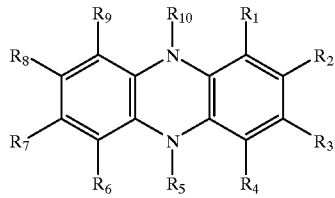

where
$R_1$, $R_4$, $R_6$, and $R_9$ are the same or different and are selected from the group consisting of: hydrogen and alkyl of $C_1$ to $C_{12}$;

$R_2$, $R_3$, $R_7$, and $R_8$ are the same or different and are selected from the group consisting of: hydrogen, alkenyl, alkyl of $C_1$ to $C_{12}$, aryl, substituted aryl, alkoxy, phenoxy, and halogenated alkanes of $C_1$ to $C_{12}$ with at least one of $R_2$, $R_3$, $R_7$ or $R_8$ being hydrogen;

$R_5$ and $R_{10}$ are the same or different and are selected from the group consisting of: linear and branched alkyl of $C_1$ to $C_3$; and if $R_5$ and $R_{10}$ are both linear alkyl, then
at least one of $R_2$, $R_3$, $R_7$, and $R_8$ are the same or different and are selected from the group consisting of: alkenyl, alkyl of $C_1$ to $C_{12}$, aryl, substituted aryl, alkoxy, phenoxy, and halogenated alkanes of $C_1$ to $C_{12}$, with at least one of $R_2$, $R_3$, $R_7$ or $R_8$ being hydrogen;

but if $R_5$ and $R_{10}$ are both methyl or ethel and $R_1$, $R_3$, $R_4$, $R_6$, $R_8$ and $R_9$ are hydrogen, then $R_2$ and $R_7$ are not both methyl, phenyl or methoxy;

if $R_1$–$R_2$ is benzo and $R_4$ is hydrogen, or if $R_3$–$R_4$ is benzo and $R_1$ is hydrogen, or if $R_2$–$R_3$ is benzo, then $R_5$ and $R_{10}$ are the same or different and are selected from the group consisting of: linear and branched alkyl of $C_1$ to $C_3$, and $R_6$, $R_7$, $R_8$, and $R_9$ are the same or different and are selected from the group consisting of: alkyl of $C_1$ to $C_{12}$ and hydrogen; and if $R_6$–$R_7$ is benzo and $R_9$ is hydrogen, or if $R_8$–$R_9$ is benzo and $R_6$ is hydrogen, or if $R_7$–$R_8$ is benzo, then $R_5$ and $R_{10}$ are the same or different and are selected from the group consisting of: linear and branched alkyl of $C_1$ to $C_3$, and $R_6$, $R_7$, $R_8$, and $R_9$ are the same or different and are selected from the group consisting of: alkyl and hydrogen.

2. The compound of claim 1, wherein $R_1$ $R_4$, $R_6$, and $R_9$ are the same or different and are selected from the group consisting of: hydrogen and methyl; $R_2$, $R_3$, $R_7$, and $R_8$ are the same or different and are selected from the group consisting of: methyl, phenyl, vinyl, alkoxy, phenoxy, tolyl, trifluoromethyl, and hydrogen, with at least one of $R_2$, $R_3$, $R_7$ or $R_8$ being hydrogen; $R_5$ and $R_{10}$ are the same or different and are selected from the group consisting of: methyl, ethyl and isopropyl; if either $R_5$ or $R_{10}$ is methyl or ethyl, then $R_2$ is selected from the group consisting of: methyl, phenyl, vinyl, phenoxy, tolyl, and trifluoromethyl.

3. The compound of claim 2, wherein at least one of said $R_2$, $R_3$, $R_7$, and $R_8$ is o-tolyl.

4. The compound of claim 1, wherein if $R_2$ is aryl, then $R_1$ is an alkyl of $C_1$ to $C_{12}$, or $R_3$ is selected from the group consisting of: alkyl of $C_1$ to $C_{12}$, aryl, substituted aryl, alkenyl, alkoxy, phenoxy, and halogenated alkanes of $C_1$ to $C_{12;\ if\ R3}$ is aryl, then $R_4$ is an alkyl of $C_1$ to $C_{12}$, or $R_2$ is selected from the group consisting of: alkenyl, alkyl of $C_1$ to $C_{12}$, aryl, substituted aryl, alkoxy, phenoxy, and halogenated alkanes of $C_1$ to $C_{12}$; if $R_7$ is aryl, then $R_6$ is an alkyl of $C_1$ to $C_{12}$, or $R_8$ is selected from the group consisting of: alkyl of $C_1$ to $C_{12}$, aryl, substituted aryl, alkenyl, alkoxy, phenoxy, and halogenated alkanes of $C_1$ to $C_{12}$; if $R_8$ is aryl, then $R_9$ is an alkyl of $C_1$ to $C_{12}$, or $R_7$ is selected from the group consisting of: alkyl of $C_1$ to $C_{12}$, aryl, substituted aryl, alkenyl, alkoxy, phenoxy, and halogenated alkanes of $C_1$ to $C_{12}$.

5. The compound of claim 1 having the formula selected from the group consisting of: 2-vinyl-5,10-dimethyl-5,10-dihydrophenazine; 2,7-bis(o-tolyl)-5,10-dimetbyl-5,10-dihydrophenazine; 2,3-dimethyl-7-trifluoromethyl-5,10-diethyl-5,10-dihydrophenazine; 2,3,5,10-tetramethyl-7-trifluoromethyl-5,10-dihydrophenazine; 2,3-diphenyl-5,10-dimethyl-5,10-dihydrophenazine; 2,5,10-trimethyl-3-phenyl-5,10-dihydrophenazine; 5,10-diisopropyl-5,10-dihydrophenazine; 2,3,5,10-tetramethyl-5,10-dihydrobenzo (B)phenazine; 5,10-dimethyl-5,10-dihydrobenzo(A) phenazine; 2-phenoxy-5,10-dimethyl-5,10-dihydrophenazine; 2,7-diphenoxy-5,10-dimethyl-5,10-dihydrophenazine; 1,5,10-trimethyl-2-phenyl-5,10-dihydrophenazine; and 2-phenyl-5,10-dimethyl-5,10-dihydrophenazine.

6. A one-pot method, comprising the steps of:
   (a) mixing a heterocyclic azine compound; a reducing reagent; a base; an alkylating reagent; a member of the group consisting of: a phase transfer catalyst, water or both a phase transfer catalyst and water; and a solvent in one pot;
   (b) stirring said mixture under an inert atmosphere; and
   (c) separating a compound from said mixture, wherein said heterocyclic azine compound is reduced and alkylated.

7. The method of claim 6, wherein said alkylating reagant is selected from the group consisting of alkyl halides and alkyl sulfonates.

8. The method of claim 6, wherein the temperature at which said mixture is heated is said mixture's reflux temperature.

9. The method of claim 6, wherein said solvent is an aprotic polar solvent.

10. The method of claim 6, wherein said method is used to produce the compounds of the formula:

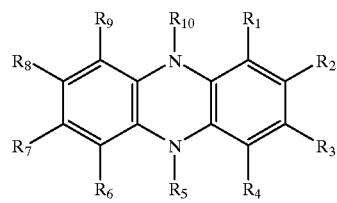

where
$R_1$, $R_4$, $R_6$ and $R_9$ are the same or different and are selected from the group consisting of: hydrogen and alkyl of $C_1$ to $C_{12}$;

$R_2$, $R_3$, $R_7$, and $R_8$ are the same or different and are selected from the group consisting of: hydrogen, alkenyl, alkyl of $C_1$ to $C_{12}$, aryl, substituted aryl, alkoxy, phenoxy, and halogenated alkanes of $C_1$ to $C_{12}$ with at least one of $R_2$, $R_3$, $R_7$ or $R_8$ being hydrogen;

$R_5$ and $R_{10}$ are the same or different and are selected from the group consisting of:

linear and branched alkyl of $C_1$ to $C_3$, and if $R_5$ and $R_{10}$ are both linear alkyl, then at least one of $R_2$, $R_3$, $R_7$, and $R_8$ are the same or different and are selected from the group consisting of: alkenyl, alkyl of $C_1$ to $C_{12}$, arvl, substituted aryl, alkoxy, phenoxy, and halogenated alkanes of $C_1$ to $C_{12}$, with at least one of $R_2$, $R_3$, $R_7$ or $R_8$ being hydrogen;

but if $R_5$ and $R_{10}$ are both methyl or ethyl and $R_1$, $R_3$, $R_4$, $R_6$, $R_8$, and $R_9$ are hydrogen, then $R_2$ and $R_7$ are not both methyl, phenyl or methoxy;

if $R_1$–$R_2$ is benzo and $R_4$ is hydrogen, or if $R_3$–$R_4$ is benzo and $R_1$ is hydrogen, or if $R_2$–$R_3$ is benzo, then $R_5$ and $R_{10}$ are the same or different and are selected from the group consisting of: linear and branched alkyl of $C_1$ to $C_3$ and $R_6$, $R_7$, $R_8$ and $R_9$ are the same or different and are selected from the group consisting of: alkyl of $C_1$ to $C_{12}$ and hydrogen; and if $R_6$–$R_7$ is benzo and $R_9$ is hydrogen, or if $R_8$–$R_9$ is benzo and $R_6$ is hydrogen, or if $R_7$–$R_8$ is benzo, then $R_5$ and $R_{10}$ are the same or different and are selected from the group consisting of: linear and branched alkyl of $C_1$ to $C_3$; and $R_6$, $R_7$, $R_8$, and $R_9$ are the same or different and are selected from the group consisting of: alkyl and hydrogen.

11. The method of claim 6, wherein said method is used to produce the compounds selected from the group consisting of: 2-vinyl-5,10-dimethyl-5 10-dihydrophenazine: 2,7-bis(o-tolyl)-5,10-dimethyl-5,10-dihydrophenazine; 2,3-dimethyl-7-trifluoromethyl-5,10-diethyl-5,10-dihydrophenazine; 2,3,5,10-tetramethyl-7-trifluoromethyl-5,10-dihydrophenazine, 2,3-diphenyl-5,10-dimethyl-5,10-dihydrophenazine; 2,5,10-trimethyl-3-phenyl-5,10-dihydrophenazine; 5,10-diisopropyl-5,10-dihydrophenazine; 2,3,5,10-tetramethyl-5,10-dihydrobenzo(B)phenazine; 5,10-dimethyl-5,10-dihydrobenzo(A)phenazine; 2-phenoxy-5,10-dimethyl-5,10-dihydrophenazine; 2,7-diphenoxy-5,10-dimethyl-5,10-dihydrophenazine; 1,5,10-trimethyl-2-phenyl-5,10-dihydrophenazine; 2-phenyl-5,10-dimethyl-5,10-dihydrophenazine; and 2,7-diphenyl-5,10-dimethyl-5,10-dihydrophenazine.

12. The method of claims 6, wherein said compound having linked heteroatoms is selected from the group consisting of phenazines, triphenodithiazines, triphenodioxazines, quinoxalinophenazines, phenoxazine-based dyes, and phenothiazine-based dyes.

13. The method of claim 6, wherein said stirring step includes the application of heat to said mixture.

14. The method of claim 6, where said separating step comprises the steps of adding water and filtering off said alkylated and reduced compound.

15. The method of claim 6, where said water is less than about 20 volume percent of said mixture and where said phase transfer catalyst is methyltributyl ammonium chloride and is present at about 0.1 molar percent of said mixture.

16. The method of claim 6, where said phase transfer is an accessible quaternary ammonium salt.

17. The method of claim 6, where said base is a metal carbonate salt.

18. The method of claim 6, where said the reducing agent is selected from the group consisting of: sodium dithionite and hypophosphorous acid.

19. The method of claim 6, where said heterocyclic azine compound is selected from the group comprising phenazines, triphenodithiazines, triphenodioxazines, quinoxalinophenazines, phenazine-based dyes, phenoxazine-based dyes, and phenothiazine-based dyes.

20. A two-phase one-pot method, comprising the steps of:
(a) mixing a heterocyclic azine compound; a reducing reagent; a base; an alkylating reagent; a member of the group consisting of: a phase transfer catalyst, water, or both a phase transfer catalyst and water; and a non-polar solvent in one pot;
(b) stirring said two-phase mixture under an inert atmosphere; and
(c) separating a compound from said two-phase mixture, wherein said heterocyclic azine compound is reduced and alkylated.

* * * * *